US011020166B2

(12) United States Patent
Batchelor et al.

(10) Patent No.: US 11,020,166 B2
(45) Date of Patent: Jun. 1, 2021

(54) MULTIFUNCTIONAL MEDICAL DEVICE

(71) Applicant: Gyrus ACMI, Inc., Southborough, MA (US)

(72) Inventors: Kester J. Batchelor, Mound, MN (US); Richard J. Curtis, Maple Grove, MN (US); Christopher A. Cook, New York, NY (US); Eric Kurtycz, Northborough, MA (US)

(73) Assignee: Gyrus Acmi, Inc., Southborough, MA (US)

( * ) Notice: Subject to any disclaimer, the term of this patent is extended or adjusted under 35 U.S.C. 154(b) by 863 days.

(21) Appl. No.: 14/865,420

(22) Filed: Sep. 25, 2015

(65) Prior Publication Data

US 2017/0086915 A1    Mar. 30, 2017

(51) Int. Cl.
*A61B 18/14* (2006.01)
*A61B 18/16* (2006.01)
(Continued)

(52) U.S. Cl.
CPC .......... *A61B 18/14* (2013.01); *A61B 18/1445* (2013.01); *A61B 18/16* (2013.01);
(Continued)

(58) Field of Classification Search
CPC ... B03C 3/38; A61B 18/16; A61B 2018/1213; A61B 2018/122
See application file for complete search history.

(56) References Cited

U.S. PATENT DOCUMENTS 4,542,461 A    9/1985  Gehike
5,669,904 A    9/1997  Platt, Jr. et al.
(Continued)

FOREIGN PATENT DOCUMENTS

CN    102470009 A    5/2012
CN    103930212 A    7/2014
(Continued)

OTHER PUBLICATIONS

Third-party submission filed on Dec. 19, 2018 for U.S. Appl. No. 15/747,905.
European Office Action for European Application No. 16778611.0; dated Dec. 3, 2018.
"U.S. Appl. No. 15/747,905, Preliminary Amendment filed Jan. 26, 2018", 10 pgs.
(Continued)

*Primary Examiner* — Michael F Peffley
*Assistant Examiner* — Bo Ouyang
(74) *Attorney, Agent, or Firm* — Schwegman Lundberg & Woessner, P.A.

(57) ABSTRACT

Disclosed is a multifunctional medical device, apparatus or system that is capable of performing a surgical procedure or operation and also capable of removing or reducing smoke particles generated by the surgical procedure or operation on a subject, the apparatus comprising a plurality of electrodes, two of which are configured to be in electrical communication with or being electrically connectable to opposite poles of a source of high voltage dc electricity to ionize, and remove or reduce smoke particles, and at least one of which is also configured to be part of a RF circuit to perform a surgical procedure or operation such as tissue cutting, cauterization, tissue sealing or coagulating at a surgical site on the subject. Also disclosed is a method of employing the above disclosed device, apparatus or system or variations thereof to perform a surgical procedure or operation at a surgical site and to remove or reduce smoke particles generated during the surgical procedure or operation.

12 Claims, 16 Drawing Sheets

(51) Int. Cl.
*A61B 18/12* (2006.01)
*A61B 18/00* (2006.01)

(52) U.S. Cl.
CPC ............ *A61B 2018/00577* (2013.01); *A61B 2018/00601* (2013.01); *A61B 2018/122* (2013.01); *A61B 2018/124* (2013.01); *A61B 2018/1213* (2013.01); *A61B 2018/1253* (2013.01); *A61B 2018/1266* (2013.01); *A61B 2018/1425* (2013.01); *A61B 2018/1467* (2013.01); *A61B 2218/008* (2013.01)

(56) References Cited

U.S. PATENT DOCUMENTS

| | | | |
|---|---|---|---|
| 6,213,999 | B1 | 4/2001 | Platt, Jr. et al. |
| 6,623,544 | B1 | 9/2003 | Kaura |
| 9,308,366 | B2 † | 4/2016 | Warren |
| 9,925,372 | B2 | 3/2018 | Amoah et al. |
| 2003/0130658 | A1 | 7/2003 | Goble et al. |
| 2004/0030330 | A1 | 2/2004 | Brassell et al. |
| 2004/0116918 | A1 | 6/2004 | Konesky |
| 2005/0171528 | A1 | 8/2005 | Sartor et al. |
| 2006/0025757 | A1* | 2/2006 | Heim ............ A61B 18/1402 606/32 |
| 2006/0217706 | A1* | 9/2006 | Lau ............ A61B 17/29 606/45 |
| 2007/0299439 | A1 † | 12/2007 | Latterell |
| 2008/0108985 | A1* | 5/2008 | Konesky ............ A61B 18/042 606/27 |
| 2010/0100091 | A1 | 4/2010 | Truckai |
| 2011/0295250 | A1* | 12/2011 | Johnson ............ A61B 18/042 606/41 |
| 2011/0306006 | A1* | 12/2011 | Holbeche ............ A61B 18/042 433/32 |
| 2012/0065635 | A1 | 3/2012 | Konesky |
| 2012/0067212 | A1* | 3/2012 | Warren ............ A61B 18/00 95/57 |
| 2012/0116384 | A1* | 5/2012 | Truckai ............ A61B 18/1477 606/33 |
| 2013/0074790 | A1 | 3/2013 | Rabhi |
| 2014/0005663 | A1 | 1/2014 | Heard et al. |
| 2014/0228836 | A1* | 8/2014 | Amoah ............ A61B 18/04 606/34 |
| 2014/0249557 | A1* | 9/2014 | Koch, Jr. ............ A61B 17/072 606/170 |
| 2014/0276795 | A1 | 9/2014 | Batchelor et al. |
| 2014/0303615 | A1 | 10/2014 | Amoah |
| 2014/0364844 | A1* | 12/2014 | Van Wyk ............ A61B 18/1477 606/37 |
| 2015/0182708 | A1 | 7/2015 | Barnard |
| 2015/0201999 | A1 | 7/2015 | Hassler, Jr. |
| 2017/0151012 | A1 | 6/2017 | Griffiths et al. |
| 2018/0014316 | A1 | 1/2018 | Guo et al. |
| 2018/0206905 | A1 | 7/2018 | Batchelor et al. |

FOREIGN PATENT DOCUMENTS

| | | |
|---|---|---|
| CN | 108024829 A | 5/2018 |
| EP | 2531132 A1 | 12/2012 |
| EP | 3324868 A1 | 5/2018 |
| EP | 3324868 B1 | 5/2020 |
| JP | H05184589 A | 7/1993 |
| JP | H09503423 A | 4/1997 |
| JP | 2001137319 A | 5/2001 |
| JP | 2012533380 A | 12/2012 |
| JP | 2014534870 A | 12/2014 |
| JP | 2018528011 A | 9/2018 |
| JP | 6585834 B2 | 10/2019 |
| WO | WO 96/09118 | 3/1996 |
| WO | 96/27337 A1 | 9/1996 |
| WO | 99/15091 A1 | 4/1999 |
| WO | 2008135736 † | 11/2008 |
| WO | WO-2008135736 A1 | 11/2008 |
| WO | 2011010148 † | 1/2011 |
| WO | WO-2011010148 A2 | 1/2011 |
| WO | 2013/045866 A2 | 4/2013 |
| WO | 2014152059 † | 9/2014 |
| WO | WO-2014152059 A1 | 9/2014 |
| WO | 2016/024130 A1 | 2/2016 |
| WO | WO-2017053945 A1 | 3/2017 |

OTHER PUBLICATIONS

"European Application Serial No. 16778611.0, Response filed Apr. 30, 2018 to Communication Pursuant to Article 94(3) EPC dated Dec. 3, 2018", 60 pgs.

"International Application Serial No. PCT/US2016/053717, International Preliminary Report on Patentability dated Apr. 5, 2018", 9 pgs.

"International Application Serial No. PCT/US2016/053717, International Search Report dated Dec. 9, 2016", 5 pgs.

"International Application Serial No. PCT/US2016/053717, Written Opinion dated Dec. 9, 2016", 7 pgs.

"Japanese Application Serial No. 2018-51489, Amendment filed Mar. 20, 2018", W/ English Translation, 7 pgs.

"Japanese Application Serial No. 2018-514989, Amendment filed Apr. 3, 2018", W/ English Translation, 27 pgs.

"Japanese Application Serial No. 2018-514989, Notice of Reason for Rejection dated Jan. 29, 2019", W/English Translation, 8 pgs.

"Japanese Application Serial No. 2018-514989, Response filed May 30, 2019 to Notice of Reason for Rejection dated Jan. 29, 2019", W/ English Translation, 42 pgs.

"Third party submission filed on Nov. 29, 2017 U.S. Appl. No. 14/865,420", 24 pgs.

"Chinese Application Serial No. 201680054565.5, Office Action dated Apr. 3, 2020", w/ English translation, 18 pgs.

"Chinese Application Serial No. 201680054565.5, Response Filed Jun. 10, 2020 to Office Action dated Apr. 3, 2020", w/ English Claims, 66 pgs.

"European Application Serial No. 16778611.0, Intention to Grant dated Jan. 16, 2020", 138 pgs.

"Japanese Application Serial No. 2019-161878, Amendment filed Oct. 3, 2019", W/English Translation, 26 pgs.

"U.S. Appl. No. 15/747,905, Non Final Office Action dated Jan. 7, 2021", 13 pgs.

"Chinese Application Serial No. 201680054565.5, Office Action dated Aug. 17, 2020", w/ English Translation, 15 pgs.

"Chinese Application Serial No. 201680054565.5, Response filed Oct. 15, 2020 to Office Action dated Aug. 17, 2020", w/ English Claims, 17 pgs.

"European Application Serial No. 20178054.1, Extended European Search Report dated Oct. 29, 2020", 6 pgs.

"Japanese Application Serial No. 2019-161878, Notification of Reasons for Rejection dated Dec. 22, 2020", w/ English Translation, 12 pgs.

"U.S. Appl. No. 15/747,905, Response filed Jan. 21, 2021 to Non Final Office Action dated Jan. 7, 2021", 13 pgs.

"Europen Application Serial No. 16778611.0, Notice of Opposition dated Mar. 31, 2021", 23 pgs.

"Japanese Applicatian Serial No. 2019-161878, Response filed Mar. 10, 2021 to Notification of Reasons for Rejection dated Dec. 22, 2020", w/English Claims, 18 pgs.

\* cited by examiner
† cited by third party

MULTIFUNCTIONAL MEDICAL DEVICE

FIELD

The embodiments of this disclosure relate generally to a multifunctional medical device, apparatus or system that provides the capability to medical personnel to accomplish multiple surgical procedures or operations in a single instrument. More particularly, the embodiments of this disclosure relate to a medical device that is capable of performing a surgical procedure or operation on a subject and also capable of reducing or removing particles generated during or following the surgical procedure or operation. Even more particularly, the embodiments of this disclosure relate to a multifunctional surgical smoke extractor for the reduction or removal of smoke particles generated during or following a procedure such as a laparoscopic or other intracorporeal procedures or open surgery on a subject. The present disclosure also relates to methods of employing such a multifunctional medical device, apparatus or system or extractor to reduce or remove smoke particles generated during or following a surgical procedure or operation on a subject.

BACKGROUND

Particles such as smoke particles are often generated during surgical procedures. Smoke particles generated in this way obscure the view of a surgeon performing the procedure and may also be hazardous to the health of the surgical staff. Development of smoke removal methods for conventional surgery has concentrated on removing the smoke by means of a vacuum and then venting the smoke externally of the operating theatre and/or filtering out the smoke particles. When laparoscopic procedures are carried out, gas is introduced into the patient via access ports to inflate an area of interest of the patient's body. Smoke generated in the insufflated area, for example when diathermic or electrocautery cutting is undertaken, is sucked out and may then be filtered. The smoke particles should be filtered out but often, in practice, they are not. Filters for such vacuum smoke removal are expensive. Often the smoke is left to permeate into the operating theatre in many procedures, causing undesirable health conditions.

Even when cryosurgery is employed, frozen vapour, droplets, or matter can be generated like fog, which is suspended in the local atmosphere. The fog too can obscure the surgeon's view and therefore may be hazardous.

US patent application publication US 2012/0,067,212 describes a surgical version of an electrostatic smoke precipitation system where an ionization wand is placed into a laparoscopic environment with an attempt to ionize the particles created by energy devices. The disclosed ionization wand is provided with a high voltage negative charge that is passed to the particles. The ionized particles are then attracted to the patient abdominal wall, via a positively charged grounding pad attached to the patient in the same way as a monopolar pad is used in monopolar electrosurgery.

US patent application publication US 2014/0,228,836 discloses an apparatus and method for removing or reducing the number of particles in an enclosed atmosphere during intracorporeal procedures. The disclosed apparatus comprises a housing adapted to be placed against the body on which a procedure is to be formed, a first electrode external to the housing for contacting the body, an elongated electrically insulated probe extending from the housing and being insertable into an intracorporeal body cavity in which a procedure is to be performed, a second electrode at the free end of the probe, and circuit means for generating voltage between said first and second electrodes. The disclosed method comprises applying a voltage between the electrodes sufficient to cause local ionization of particles within the body cavity such that they migrate away from the second electrode, thereby removing or reducing the number of particles generated during the procedure from the enclosed atmosphere at or around the site of the procedure.

SUMMARY

In an embodiment, the present disclosure provides a multifunctional medical device comprising a first electrode and a second electrode wherein the first electrode and the second electrode are configured to be in electrical communication with or electrically connectable to opposite poles of a source of high voltage dc electricity to form a dc circuit to ionize, and remove or reduce smoke particles generated at a surgical site on a subject, and wherein the first or the second electrode is also configured to be in electrical communication with or electrically connectable to a source of surgical radio frequency energy to form a RF circuit to perform a surgical procedure or operation on the subject. In an embodiment, the device further comprises means to control and/or monitor the dc circuit. In an embodiment, the device further comprises means to control and/or monitor the RF circuit. In an embodiment, the first electrode may be configured to be used both as an ionizing electrode in the dc circuit and as a cutting electrode in the RF circuit as well. In an embodiment, the second electrode may also be configured as a RF current return pad in the RF circuit. In an embodiment, the device may further comprise a RE current return pad in the RF circuit.

In an embodiment, the present disclosure provides a multifunctional medical device or system comprising a source of high voltage dc electricity; a first electrode; and a second electrode; wherein the first electrode and the second electrode are configured to be in electrical communication with or electrically connectable to opposite poles of the source of high voltage dc electricity to form a dc circuit to ionize, and reduce or remove smoke particles generated at a surgical site on a subject, and wherein the first or the second electrode is also configured to be in electrical communication with or electrically connectable to a source of surgical radio frequency energy to form a RF circuit to perform a surgical procedure or operation on the subject. In an embodiment, the device or system further comprises means to control and/or monitor the dc circuit. In an embodiment, the device or system further comprises means to control and/or monitor the RF circuit. In an embodiment, the first electrode may be configured to be used as an ionizing electrode in the dc circuit and as a tissue cutting blade in the RF circuit as well. In an embodiment, the device or system may further comprise a RF circuit current return pad. In an embodiment, the first electrode or the second electrode may be configured to be used as a RF current return pad in the RF circuit and also as a smoke particle collecting patch in the dc circuit. In an embodiment where the RF current return pad is used as a smoke particle collecting patch in the dc circuit, the first electrode may then be configured to be used as an ionizing electrode in the dc circuit. In an embodiment, the dc circuit further comprises a RF isolation transformer for removing or eliminating any undesired RF current to prevent any hazard or damage to the subject under the surgical procedure or operation. In an embodiment, the second electrode may be configured to be used as a monopolar cutting blade in the RF circuit. In an embodiment, the medical device or system may further comprise a source of surgical radio frequency energy.

In an embodiment, the present disclosure provides a multifunctional medical device comprising a first electrode; a second electrode; and a third electrode; wherein the first electrode and the second electrode are configured to be in electrical communication with or electrically connectable to opposite poles of a source of high voltage dc electricity to form a dc circuit to ionize, and remove or reduce smoke particles generated at a surgical site on a subject, and wherein the third electrode is configured to be in electrical communication with or electrically connectable to a source of surgical radio frequency energy to form a RF circuit to perform a surgical procedure or operation on the subject. In an embodiment, the device further comprises means to control and/or monitor the dc circuit. In an embodiment, the device or system further comprises means to control and/or monitor the RF circuit. In an embodiment, the first electrode may also be configured to be in communication with the third electrode in the RF circuit. In an embodiment, the device may further comprise a RF current return pad.

In an embodiment, the present disclosure provides a multifunctional medical device or system comprising a source of high voltage dc electricity; a first electrode; a second electrode; and a third electrode; wherein the first electrode and the second electrode are configured to be in electrical communication with or electrically connectable to opposite poles of the source of high voltage dc electricity to form a dc circuit to ionize, and remove or reduce smoke particles generated at a surgical site on a subject, and wherein the first electrode or the second electrode is also configured to be in electrical communication with or electrically connectable to a source of surgical radio frequency energy and the third electrode to form a RF circuit to perform a surgical procedure or operation on the subject. In an embodiment, the device or system further comprises means to control and/or monitor the dc circuit. In an embodiment, the device or system further comprises means to control and/or monitor the RE circuit. In an embodiment, the surgical procedure or operation is tissue sealing or tissue coagulation. In an embodiment, the dc circuit further comprises a RF isolation transformer for removing or eliminating any undesired RF current to prevent any hazard or damage to the subject under the surgical procedure or operation. In an embodiment, the second electrode may be configured to be in electrical communication with or electrically connectable to a source of surgical radio frequency energy and the third electrode to form a RF circuit to perform tissue sealing or coagulation at a surgical site. In an embodiment, the medical device or system further comprises a source of surgical radio frequency energy.

In an embodiment, the present disclosure provides a multifunctional medical device comprising a first electrode; a second electrode; a third electrode; and a fourth electrode; wherein the first electrode and the second electrode are configured to be in electrical communication with opposite poles of a source of high voltage dc electricity to ionize, and remove or reduce smoke particles generated at a surgical site on a subject, and wherein the third electrode and the fourth electrode are configured to be in communication with a source of surgical radio frequency energy to form a RF circuit to perform a surgical procedure or operation on the subject. In an embodiment, the device further comprises means to control and/or monitor the dc circuit. In an embodiment, the device or system further comprises means to control and/or monitor the RF circuit. In an embodiment, the first electrode may also be configured to be in communication with the RF circuit.

In an embodiment, the present disclosure provides a multifunctional medical device or system comprising a source of high voltage dc electricity; a first electrode; a second electrode; a third electrode; and a fourth electrode; wherein the first electrode and the second electrode are configured to be in electrical communication with or electrically connectable to opposite poles of the source of high voltage dc electricity to ionize, and reduce or remove smoke particles generated at a surgical site on a subject; and wherein the third electrode and the fourth electrode are configured to be in communication with or electrically connectable to a source of surgical radio frequency energy to form a RF circuit to perform a surgical procedure or operation on the subject. In an embodiment, the medical device or system further comprises means to control and/or monitor the dc circuit. In an embodiment, the medical device or system further comprises means to control and/or monitor the RF circuit. In an embodiment, the first electrode or the second electrode is also configured to be in communication with or electrically connectable to the third electrode or the fourth electrode to form a RF circuit to perform tissue cutting. In an embodiment, the third electrode and the fourth electrode are configured to form a RF circuit to seal or coagulate tissues. In an embodiment, the dc circuit further comprises a RF isolation transformer for removing or eliminating any undesired RF current to prevent any hazard or damage to the subject under the surgical procedure or operation. In an embodiment, the medical system may further comprise a source of surgical radio frequency energy.

In all the above embodiments, the source of high voltage dc electricity may be from a mains power supply through a transformer and associated dc rectifier. It may also be generated remotely or may be from an outside electricity source. It may also be from a battery pack. In an embodiment, the battery pack may be detachable, removable, or separable from the device or system. In an embodiment, the battery pack may be housed within the device. In an embodiment, the battery pack may be rechargeable. In an embodiment where the source of high voltage dc electricity is from a rechargeable battery pack, it may be recharged directly through contact with electrical conductors or indirectly by electromagnetic induction. In another embodiment, the source of high voltage dc electricity may be conveniently housed within the medical device. It may also be provided in other manners known in the art.

In all the above embodiments, the medical device or system further comprises a dc electricity controller and/or monitor to control and/or monitor the current circulating in the dc circuit to be within a safe limit. In all the above embodiments, the medical device or system further comprises a RF current or voltage controller and/or monitor to control and/or monitor the current or voltage in the RF circuit to maintain the safety and/or the different functions of the RF circuit.

In an embodiment, the dc circuit of the medical device or system may be configured to be operable simultaneously, concurrently, alternatively, intermittently, or sequentially with the RF circuit to ionize and remove or reduce smoke particles while the RF circuit is turned on to perform a surgical procedure or operation. In an embodiment, the electrical communication of the electrodes in the dc circuit and the electrical communication of the electrodes in the RF circuit may be turned on simultaneously, concurrently, alternatively, intermittently, or sequentially. In some embodiments, the dc circuit may be turned on during or after a surgical procedure or operation.

In another embodiment, the medical device may be a standalone smoke extractor comprising an elongated member having a proximal end, a distal end, an outer surface, and a lumen extending through the elongated member; a first electrode attached to the distal end of the elongated member; a second electrode disposed over the outer surface of the elongated member; and a handle attached to the proximal end of the elongated member; wherein the first electrode and the second electrode are configured to be in electrical communication with or electrically connectable to opposite poles of a source of high voltage dc electricity. In an embodiment, the first electrode is configured to be longitudinally movable along the lumen of the elongated member. In an embodiment, the smoke extractor further comprises means to control and/or monitor the dc circuit. In an embodiment, the means to control and/or monitor the dc circuit is disposed in the handle. In an embodiment, the smoke extractor further comprises a source of high voltage dc electricity disposed in the handle. In an embodiment, the source of the high voltage dc electricity is in the form of a detachable battery pack positionable in the handle portion of the extractor. In an embodiment, the first electrode is configured to be the particle ionizing electrode and the second electrode is configured to be the particle collecting electrode. In an embodiment, the elongated member is configured to be tubular for easy insertion through an access port into a surgical site on a subject.

In a further embodiment, the present disclosure also provides a method of removing or reducing smoke related particles during a surgical procedure or operation on a subject, the method comprising providing a source of high voltage dc electricity; providing a device or system according to any one of the above described disclosure and variations thereof, properly connecting the device or system with the source of high voltage dc electricity; properly positioning the device at a surgical site of a subject where a surgical procedure is to be performed, and properly turning on the device or the system to ionize smoke particles towards one electrode of the device and attract the ionized smoke particles towards the other electrode of the device to remove or reduce the smoke particles from the surgical site of the subject.

In another embodiment, the present disclosure provides a method of removing or reducing smoke related particles during a surgical operation on a subject, the method comprising providing a source of high voltage dc electricity; providing a device or a system according to any one of the above described disclosure and variations thereof wherein the device or system has two electrodes in the dc circuit; properly connecting the two electrodes with the device or the system; properly positioning the two electrodes of the device into a surgical site where a surgical procedure is to be performed; and properly turning on the device or the system to ionize smoke particles towards one electrode of the device and attract the ionized smoke particles towards the other electrode of the device to remove or reduce the smoke particles from the surgical site of the subject.

DETAILED DESCRIPTION

Figure 1:
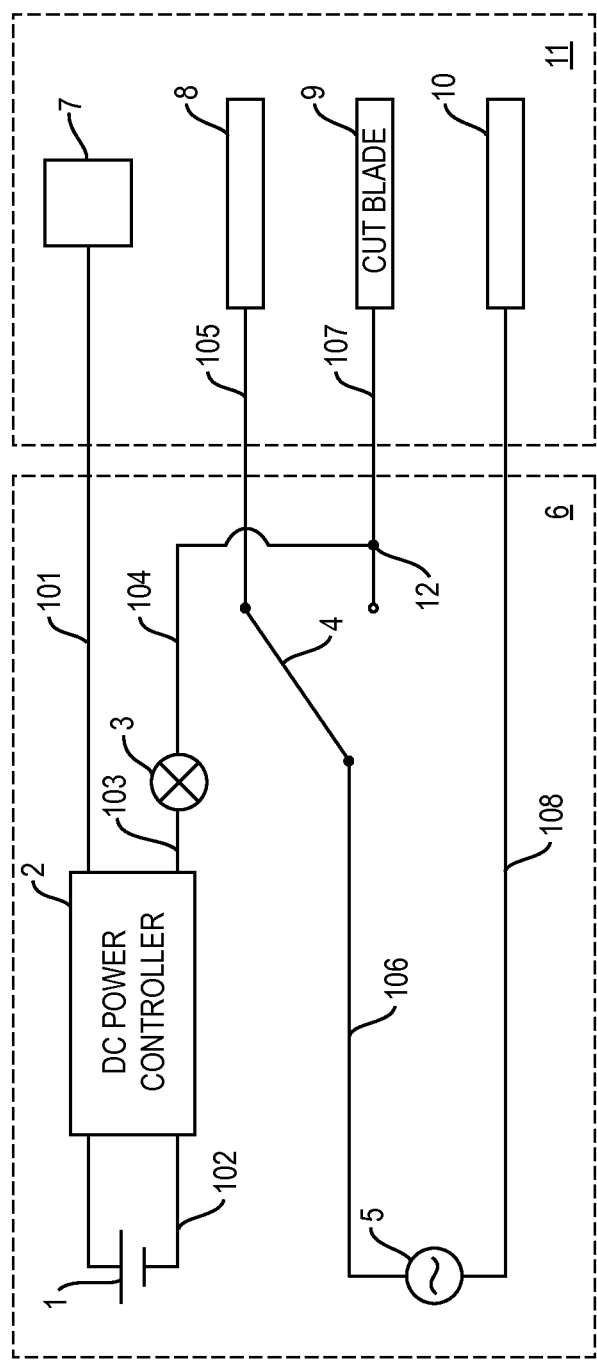
FIG. 1 is a schematic representation of a device or system in accordance with one embodiment of the present disclosure wherein one electrode is configured to perform smoke particle ionization in the dc circuit and tissue cutting in the RF circuit.

The explanations and illustrations presented herein are intended to acquaint others skilled in the art with the disclosure, its principles, and its practical applications. Those skilled in the art may adapt and apply the disclosure in numerous forms, as may be best suited to the requirements of a particular use. The specific embodiments of the present disclosure as set forth are not intended to be exhaustive or limiting of the invention. The scope of the invention should be determined not with reference to the above description, but should be determined with reference to the appended claims, along with the full scope of equivalents to which such claims are entitled.

The terms "one embodiment", "an embodiment", "another embodiment", "some embodiments", "other embodiments", and similar expressions indicate that the embodiment or embodiments described may include a particular feature, structure, or characteristic, but every embodiment may not necessarily include the particular feature, structure, or characteristic. Moreover, such phrases are not necessarily referring to the same embodiment. Furthermore, when a particular feature, structure, or characteristic is described in connection with an embodiment, it would be within the knowledge of one skilled in the art to incorporate such feature, structure, or characteristic into other embodiments, whether or not explicitly described, unless clearly stated to the contrary. That is, the various individual elements described below, even if not explicitly shown in a particular combination, are nevertheless contemplated as being combinable with each other to form other additional embodiments or to complement and/or enrich the described embodiment or embodiments, as would be understood by one of ordinary skill in the art.

The articles "a", "an" and "the" are used herein to refer to one or more than one (i.e. to at least one) of the grammatical object of the article unless otherwise clearly indicated by contrast. By way of example, "an element" means one element or more than one element.

The term "including" is used herein to mean, and is used interchangeably with, the phrase "including but not limited to". The term "or" is used herein to mean, and is used interchangeably with, the term "and/or", unless context clearly indicates otherwise.

The term "such as" is used herein to mean, and is used interchangeably, with the phrase "such as but not limited to". Unless specifically stated or obvious from context, as used herein, the term "about" is understood as within a range of normal acceptance in the art, for example within standard deviations of the mean.

In this specification the terms such as "particles", "smoke", "fog", "smoke particles", and related terms are intended to encompass any particles, or molecules or matter suspended in an atmosphere including suspended droplets formed by heat or cold.

In this specification, the term "a dc circuit" means that the components of the circuit are powered by a source of direct current voltage electricity. It does not mean it is a closed system. It may comprise further components in addition to those explicitly indicated ones. It is mainly used throughout the specification for the purpose of differentiating it from a RF circuit where a radio frequency energy source is used.

In this specification, the term "a RF circuit" means that the components of the circuit are powered by a source of surgical radio frequency energy. It does not mean it is a closed system. It may comprise further components in addition to those explicitly indicated ones. It is mainly used throughout the specification for the purpose of differentiating it from a dc circuit where a direct current (dc) electricity energy source is used.

In an embodiment, the present disclosure provides a multifunctional medical device comprising a first electrode and a second electrode wherein the first electrode and the second electrode are configured to be in electrical communication with or electrically connectable to opposite poles of a source of high voltage dc electricity to form a dc circuit to ionize, and remove or reduce smoke particles generated at a surgical site on a subject, and wherein the first or the second electrode is also configured to be in electrical communication with or electrically connectable to a source of surgical radio frequency energy to form a RF circuit to perform a surgical procedure on the subject. In an embodiment, the device further comprises means to control and/or monitor the dc circuit. In an embodiment, the device further comprises means to control and/or monitor the RF circuit. In an embodiment, the first electrode may be configured to be used both as an ionizing electrode in the dc circuit and as a cutting electrode in the RF circuit as well. In an embodiment, the second electrode may also be configured as a RE current return pad in the RF circuit. In an embodiment, the device may further comprise a RF current return pad in the RF circuit.

In an embodiment, the present disclosure provides a multifunctional medical device or system comprising a source of high voltage dc electricity; a first electrode; and a second electrode; wherein the first electrode and the second electrode are configured to be in electrical communication with or electrically connectable to opposite poles of the source of high voltage dc electricity to form a dc circuit to ionize, and reduce or remove smoke particles, and wherein the first or the second electrode is also configured to be in communication with or electrically connectable to a source of surgical radio frequency energy to form a RF circuit to perform a surgical procedure or operation. In an embodiment, the device or system further comprises means to control and/or monitor the dc circuit. In an embodiment, the device or system further comprises means to control and/or monitor the RF circuit. In an embodiment, the first electrode may be configured to be used as an ionizing electrode in the dc circuit and as a tissue cutting blade in the RF circuit as well. In an embodiment, the device may further comprise a RF current return pad. In an embodiment, the RF current return pad may also be configured to be used as a smoke particle collecting patch in the dc circuit to remove or reduce smoke particles from the surgical site. In an embodiment where the RF current return pad is used as a smoke particle collecting patch in the dc circuit, the first electrode is then configured to be used as an ionizing electrode in the dc circuit. In an embodiment, the dc circuit further comprises a RF isolation transformer for removing or eliminating any undesired RF current to prevent any hazard or damage to the subject under the surgical procedure or operation. In an embodiment, the second electrode may be configured to be used as a monopolar cutting blade in the RE circuit. In an embodiment, the medical system further comprises a source of surgical radio frequency energy.

In an embodiment where the first electrode is configured to be used as an ionizing electrode to ionize smoke particles, the second electrode is then configured to be used as a smoke particle collecting electrode to attract and collect the ionized smoke particles towards the second electrode, and consequently removing or reducing smoke particles from the surgical site. In this embodiment, the second electrode is configured to have a large surface area in order to facilitate the collection of the ionized smoke particles. In this embodiment, both of the first and the second electrodes may be configured to be positionable at or near the surgical site. In this embodiment, the second electrode may be disposed over the first electrode with insulating material to separate the two electrodes from direct physical contacts. The insulating material may be $Al_2O_3$, boron nitride, porcelain, steatite, zirconia, PTFE, reinforced mica, silicon rubber, or other ceramic materials such as disclosed in U.S. Pat. Nos. 3,970,088 and 6,942,662. In this embodiment, the second electrode may be made to be tubular. In this embodiment, the first electrode may be a needle or lancet type of electrode for better ionization.

It would be appreciated that methods and materials for manufacturing different types of electrodes are well known in the art, for example, as disclosed in U.S. Pat. Nos. 4,862,890, 4,958,539, 8,357,155, and 8,852,183. It should be understood that all the electrodes described throughout this disclosure may be similarly made. Consequently, no further additional descriptions of electrodes will be attempted for subsequent sections unless otherwise specifically indicated.

In an embodiment where the first electrode in the dc circuit is configured to be used as a smoke particle collecting patch in the dc circuit and as the RF current return pad in the RF circuit, the second electrode in the dc circuit is then configured to be used as a smoke particle ionizing electrode. The second electrode may also be configured to be used as a cutting blade for cutting tissues. In this embodiment, the RF current return pad may be made separate or detachable from the site of the surgical procedure or operation. In this embodiment, the RF current return pad may be positioned away from the surgical site such as under the skin of the subject.

In an embodiment where the electrode is configured to be used as a cutting blade, smoke particles may be produced during the cutting process. These smoke particles may be ionized and removed or reduced by the electrodes in the dc circuit disposed in the same device. In an embodiment, the dc circuit may be powered by a battery pack. In an embodiment, the battery pack may be detachable or rechargeable.

In an embodiment, the present disclosure provides a multifunctional medical device comprising a handle member; an elongated member attached to the handle member, the elongated member having a proximal end, a distal end, an outer surface, and a lumen extending through the elongated member; a first electrode disposed inside the lumen of the elongated member; and a second electrode disposed over the outer surface of the elongated member; wherein the first electrode and the second electrode are configured to be in electrical communication with or electrically connectable to opposite poles of a source of high voltage dc electricity to form a dc circuit to ionize, and to reduce or remove smoke particles, and wherein the first electrode is also configured to be in electrical communication with or electrically connectable to a source of surgical radio frequency energy to form a RF circuit to perform a surgical procedure or operation. In an embodiment, the medical device further comprises means to control and/or monitor the dc circuit. In an embodiment, the medical device further comprises means to control and/or monitor the RF circuit. In an embodiment, the device may further comprise a source of high voltage dc electricity detachably positioned inside the handle member. In an embodiment, the second electrode may be configured to be a smoke particle collecting electrode. In an embodiment, the second electrode may be configured to cover most of the surface area of the elongated member. In an embodiment, the first electrode may be made to be movable along the elongated member. In an embodiment, the device may be capable of performing tissue cutting. In an embodiment, the device may be capable of performing monopolar tissue cutting. In an embodiment where the first electrode is configured to be used in the dc circuit to ionize smoke particles, it may also be configured to be used as a cutting blade in the RF circuit to perform tissue cutting. In an embodiment, the device may further comprise a RF current return pad external to the handle.

In an embodiment, the present disclosure provides a multifunctional medical device comprising a first electrode; a second electrode; and a third electrode; wherein the first electrode and the second electrode are configured to be in electrical communication with or electrically connectable to opposite poles of a source of high voltage dc electricity to form a dc circuit to ionize, and remove or reduce smoke particles generated at a surgical site on a subject, and wherein the third electrode is configured to be in electrical communication with or electrically connectable to a source of surgical radio frequency energy to form a RF circuit to perform a surgical procedure on the subject. In an embodiment, the medical device further comprises means to control and/or monitor the dc circuit. In an embodiment, the medical device further comprises means to control and/or monitor the RF circuit. In an embodiment, the first electrode may also be configured to be in communication with the third electrode in the RF circuit. In an embodiment, the device may further comprise a RF current return pad.

In an embodiment, the present disclosure provides a multifunctional medical device or system comprising a source of high voltage dc electricity; a first electrode; a second electrode; and a third electrode; wherein the first electrode and the second electrode are configured to be in electrical communication with or electrically connectable to opposite poles of the source of high voltage dc electricity to form a dc circuit to ionize, and remove or reduce smoke particles generated at a surgical site on a subject, and wherein the first electrode or the second electrode is also configured to be in electrical communication with or electrically connectable to a source of surgical radio frequency energy and the third electrode to form a RF circuit to perform a surgical procedure or operation.

In an above embodiment, the first electrode may be configured to be used as an ionizing electrode in the dc circuit and also as a sealing electrode in the RF circuit. In an embodiment where the first electrode is configured to be used as both an ionizing electrode in the dc circuit and also as a sealing electrode in the RF circuit, the second electrode may be configured to be used as a smoke particle collecting electrode to attract and collect the ionized smoke particles towards the second electrode, thereby removing or reducing the smoke particles from the surgical site. In this embodiment, the second electrode may be made to possess a large surface area. In this embodiment, the second electrode may be disposed over the first electrode through insulating material. In this embodiment, the second electrode may be disposed over the third electrode through insulating material. In this embodiment, the second electrode may be disposed over both the first and the third electrodes through insulating material. In an embodiment, the medical device or system may further comprise a source of surgical radio frequency energy.

In an embodiment where the first electrode is configured to be used as an ionizing electrode in the dc circuit, the second electrode and the third electrode may be configured to perform tissue sealing or coagulation in the RF circuit. In an embodiment where the first electrode is configured to be used as an ionizing electrode in the dc circuit, the second electrode is then configured to be used as a smoke particle collecting patch. In an embodiment, the dc circuit further comprises a RF isolation transformer for removing or eliminating any undesired RF current in the dc circuit to prevent any hazard or damage to the subject under the surgical procedure or operation. In an embodiment, the second electrode may be configured to be in communication with the third electrode to form a RF circuit to perform a bipolar tissue sealing or tissue coagulation.

In an embodiment where an electrode is configured to be used both as a sealing electrode in the RF circuit and as a smoke particle collecting patch in the dc circuit, the electrode should be made to possess a large surface area to facilitate attraction and collection of ionized smoke particle and to more efficiently disperse the RF return current.

In an embodiment, the present disclosure provides a multifunctional medical system comprising a handle member; an elongated member having a proximal end, a distal end, and an outer surface, the proximal end of the elongated member attached to the handle member; a first electrode attached to the distal end of the elongated member; a second electrode also attached to the distal end of the elongated member; and a third electrode disposed over the outer surface of the elongated member; wherein the first electrode and the third electrode are configured to be in electrical communication with or electrically connectable to opposite poles of a source of high voltage dc electricity to form a dc circuit to ionize, and to remove or reduce smoke particles generated at a surgical site on a subject, and wherein the first electrode and the second electrode are also configured to be in electrical communication with or electrically connectable to the source of the surgical radio frequency energy to form a RE circuit to perform a surgical procedure or operation. In an embodiment, the system may further comprise a source of high voltage dc electricity detachably disposed inside the handle member. In an embodiment, the third electrode may be configured to cover the majority of the outer surface of the elongated member. In an embodiment the elongated member may be tubular. In an embodiment, the medical system may further comprise a source of surgical radio frequency energy.

In an embodiment, the present disclosure provides a multifunctional medical device comprising a first electrode; a second electrode; a third electrode; and a fourth electrode; wherein the first electrode and the second electrode are configured to be in electrical communication with opposite poles of a source of high voltage dc electricity to ionize, and remove or reduce smoke particles generated at a surgical site on a subject, and wherein the third electrode and the fourth electrode are configured to be in communication with or electrically connectable to a source of the surgical radio frequency energy to form a RF circuit to perform a surgical procedure on the subject. In an embodiment, the medical device further comprises means to control and/or monitor the dc circuit. In an embodiment, the medical device further comprises means to control and/or monitor the RF circuit. In an embodiment, the first electrode may also be configured to be in communication with the RF circuit.

In an embodiment, the present disclosure provides a multifunctional medical device or system comprising a source of high voltage dc electricity; a first electrode; a second electrode; a third electrode; and a fourth electrode; wherein the first electrode and the second electrode are configured to be in electrical communication with or electrically connectable to opposite poles of the source of high voltage dc electricity to ionize, and reduce or remove smoke particles generated at a surgical site on a subject; and wherein the third electrode and the fourth electrode are configured to be in communication with or electrically connectable to a source of surgical radio frequency energy to form a RF circuit to perform a surgical procedure or operation. In an embodiment, the medical device or system further comprises means to control and/or monitor the dc circuit. In an embodiment, the medical device or system further comprises means to control and/or monitor the RF circuit. In an embodiment, the first electrode or the second electrode may also be configured to be in communication with or electrically connectable to the third electrode or the fourth electrode to form a RF circuit to perform tissue cutting.

In an embodiment where the first electrode is configured to be used as an ionizing electrode in the dc circuit, the second electrode is configured to be used as a smoke particle collecting patch in the dc circuit. In an embodiment where the first electrode is configured to be used as an ionizing electrode in the dc circuit and also as a cutting blade in the RF circuit, the first electrode may then be configured to be in communication with either the third electrode or the fourth electrode to form a bipolar cutting device. In an embodiment, the medical system may further comprise a source of surgical radio frequency energy.

In an embodiment, the present disclosure provides a multifunctional medical device comprising a handle member; an elongated member attached to the handle member, the elongated member having a proximal end, a distal end, an outer surface, and a lumen extending though the elongated member; a first electrode attached to the distal end of the elongated member; a second electrode also attached to the distal end of the elongated member; a third electrode also attached to the distal end of the elongated member; and a fourth electrode disposed over the outer surface of the elongated member; wherein the first electrode and the second electrode are configured to be in communication with or electrically connectable to a source of surgical radio frequency energy to form a RF circuit to perform a surgical procedure or operation on a subject; and wherein the third electrode and the fourth electrode are configured to be in electrical communication with or electrically connectable to opposite poles of a source of high voltage dc electricity to ionize, and reduce or remove smoke particles generated at a surgical site on the subject. In an embodiment, the third electrode may also be configured to be in communication with or electrically connectable to the first electrode or the second electrode to perform a bipolar tissue cutting. In an embodiment, the third electrode may be configured to be movable along the elongated member. In an embodiment, the medical system may further comprise a source of surgical radio frequency energy.

In an embodiment, the source of high voltage dc electricity may be detachably positioned inside the handle member. In an embodiment, the fourth electrode may be made to cover the majority of the outer surface of the elongated member. In an embodiment, all the four electrodes may be disposed in front portion of the elongated member. In an embodiment, all the four electrodes may be disposed in the insertable front portion of the elongated member.

In all the above embodiments, the source of high voltage dc electricity may be from a mains power supply through a transformer and associated dc rectifier. It may also be generated remotely or may be from an outside electricity source. It may also be from a battery pack. In an embodiment, the battery pack may be detachable, removable, or separable from the device. In an embodiment, the battery pack may be housed within the device. In an embodiment, the battery pack may be rechargeable. In an embodiment where the source of high voltage dc electricity is from a rechargeable battery pack, it may be recharged directly through contact with electrical conductors or indirectly by electromagnetic induction. In another embodiment, the source of high voltage dc electricity may be conveniently housed within the medical device. It may still be provided in some other manners that are within the grasp of an ordinary skilled person in the art.

In all the above embodiments, the source of high voltage dc electricity is from an electrical supply within a range of about 1 kV to about 30 kV, and preferably around 5 kV to 15 kV. Although a dc voltage of up to 30 kV could be used, lower voltages will be sufficient. For example around 8 or 9 kV is envisaged, with a current limiting regulator in the form of a series resistor maintaining the current at a safe limit for the patient and operator. A clean reasonably constant voltage is preferred, but a voltage which is fluctuating could be used, particularly where the device is employed in conjunction with an electrically driven surgical tool, provided there is no current reversal. In this description 'dc' is intended to cover an oscillating or a noisy voltage which is biased to provide current only in one direction in a circuit.

In all the above embodiments, the device or the system further comprises at least one dc electricity controller or monitor to control or monitor the current circulating in the dc circuit to be within a safe limit. In order to improve safety it is envisaged that a control means will be provided to monitor the current travelling in the high voltage circuit, which will stop the flow of current very quickly should the current increase rapidly in a short space of time, i.e. should a short circuit be detected, for example where the second electrode touches the body of the patient. This will avoid or reduce accidental voltage shocks to the patient. In addition it is possible to monitor increased impedance, and thereby detect a blocked electron emission. The current regulator is capable of limiting the amount of current flowing across the high voltage dc circuit to a certain amount such as less than 10 µA, for example around 5 µA.

In all the above embodiments, the device or system further comprises at least a RF current or voltage controller or monitor to control or monitor the current or voltage in the RF circuit to maintain the safety and/or efficiency of the RF circuit.

In all the above embodiments, the dc circuit further comprises a RF isolation transformer for removing or eliminating any undesired RF current to prevent any hazard or damage to the subject under the surgical procedure or operation.

In all the above relevant embodiments, the means to control the dc circuit and the means to control the RF circuit can be easily and conveniently achieved through various control means such as in the form of knobs, touches, push buttons, slides, switches and other tools/devices such as disclosed, for example, in U.S. Pat. Nos. 5,312,327 and 5,472,442, and PCT application publication No. WO 2014/151560. These tools/devices may be handled by hand, or by foot. They may be handled remotely or automatically. The means may also be in the form of a computer or some computerized tools with the ability to control and/or monitor current or voltage both in a dc circuit and in a RF circuit.

It's to be understood throughout this disclosure that conductor or wiring lines connecting different components in the dc circuit and in the RF circuit are all insulated from each other. These lines may be isolated (e.g. each may extend from one component to another component without commonality with other lines). These lines may be joined together to minimize the lines and complexity of these cable lines necessary for connectivity. The design and construction of this type of conductor or wiring lines are well within the grasp of a skilled person in the art.

In all the above embodiments, the source of surgical radio frequency energy should have a frequency of between 100 KHz and 100 MHz for tissue cutting, tissue sealing or coagulation, or tissue cauterization. More preferable, the frequency should be between 300 kHz and 2 MHz. Different surgical RF generators are known in the art for both monopolar and bipolar purposes. These surgical RF generators are well known in the art for purposes of tissue separation or cutting, tissue coagulation or sealing, or tissue cauterization.

In an embodiment, the dc circuit of a device or system in accordance with any one of the above described or variations thereof may be configured to be operable to remove or reduce smoke particles simultaneously, concurrently, alternatively, intermittently, or sequentially while the RF circuit of the device is also in operation to perform a surgical procedure or operation. In some embodiments, the dc circuit of the device or system may be turned on during or after the surgical procedure or operation.

In another embodiment, the medical device may be a standalone smoke extractor comprising an elongated member having a proximal end, a distal end, an outer surface, and a lumen extending through the elongated member; a first electrode attached to the distal end of the elongated member; a second electrode disposed over the outer surface of the elongated member; and a handle attached to the proximal end of the elongated member; wherein the first electrode and the second electrode are configured to be in electrical communication with or electrically connectable to opposite poles of a source of high voltage dc electricity. In an embodiment, the first electrode is configured to be longitudinally movable along the lumen of the elongated member. In an embodiment, the smoke extractor further comprises means to control and/or monitor the dc circuit. In an embodiment, the means to control and/or monitor the dc circuit is disposed in the handle. In an embodiment, the smoke extractor further comprises a source of high voltage dc electricity disposed in the handle. In an embodiment, the source of the high voltage dc electricity is in the form of a detachable battery pack positionable in the handle portion of the extractor. In an embodiment, the first electrode is configured to be the particle ionizing electrode and the second electrode is configured to be the particle collecting electrode. In an embodiment, the elongated member is configured to be tubular for easy insertion through an access port into a surgical site on a subject.

In the above embodiments, the device or system may further include an introducer tool such as an endoscope, a catheter, an access sheath, or an access port.

In a further embodiment, the present disclosure also provides a method of removing or reducing smoke related particles during a surgical procedure or operation on a subject, the method comprising providing a source of high voltage dc electricity; providing a device or system according to any one of the above described disclosure and variations thereof, properly connecting the device or system with the source of high voltage dc electricity; properly positioning the device at a surgical site of a subject where a surgical procedure is to be performed, and properly turning on the device or the system to ionize smoke particles towards one electrode of the device and attract the ionized smoke particles towards the other electrode of the device to remove or reduce the smoke particles from the surgical site of the subject.

In another embodiment, the present disclosure provides a method of removing or reducing smoke related particles during a surgical operation on a subject, the method comprising providing a source of high voltage dc electricity; providing a device or a system according to any one of the above described disclosure and variations thereof wherein the device or system has two electrodes in the dc circuit; properly connecting the two electrodes with the device or the system; properly positioning the two electrodes of the device into a surgical site where a surgical procedure is to be performed; and properly turning on the device or the system to ionize smoke particles towards one electrode of the device and attract the ionized smoke particles towards the other electrode of the device to remove or reduce the smoke particles from the surgical site of the subject.

In another embodiment, the present disclosure provides a method of removing or reducing smoke related particles during a surgical operation on a subject, the method comprising providing a source of high voltage dc electricity; providing a source of surgical RF energy; providing a device or a system according to any one of the above described disclosure and variations thereof wherein the device or system has two electrodes in the dc circuit and two electrodes in the RF circuit; properly connecting the two dc electrodes of the device or the system with the source of high voltage dc electricity; properly connecting the two RF electrodes of the device or system with the source of surgical RF energy; properly positioning the device into a surgical site where a surgical procedure is to be performed; and properly actuating the RF circuit of the device or the system to perform a surgical procedure or operation wherein smoke particles are generated; and properly actuating the dc circuit of the device or system to ionize the generated smoke particles towards one dc electrode of the device and attract the ionized smoke particles towards the other dc electrode of the device or system to remove or reduce the smoke particles from the surgical site of the subject. In an embodiment, the surgical procedure or operation is performed with smoke particle reduction or removal simultaneously, concurrently, alternatively, intermittently, or sequentially.

It will be apparent to the skilled addressee that many modifications, variants and improvements are possible within the ambit of the invention defined herein. For example, a device in accordance with some embodiments as described may be employed during the extracorporeal procedure.

The principles of the present disclosure may be better understood with reference to the drawings and the accompanying descriptions, wherein like reference numerals have been used throughout to designate identical or similar elements. It should be understood that these drawings are not necessarily are drawn to scale. They are presented just for illustrative purposes only, and are not intended to limit the scope of the disclosure. Examples of materials, dimensions, and constructions are included for some elements. Those of ordinary skill in the art should understand that many of the examples provided have suitable alternatives and these alternatives should also be considered within the scope of this disclosure. Moreover, certain terminology is used herein for convenience only and is not to be taken as a limitation on the present disclosure.

FIG. 1 refers to a schematic representation of a device or system in accordance with one aspect of the present disclosure. The device or system comprises a dc circuit and a RF circuit, each of which will be illustrated in more details below.

The dc circuit in accordance with FIG. 1 includes a high voltage dc electrical source 1, a dc power controller 2, a RF isolation transformer 3, a first electrode 9, and a second electrode 7. The electrode 7 is configured to be connectable to the high voltage dc electrical source 1 through an insulated conductor or wiring line 101. The insulated conductor or wiring line 101 may just be an insulated cable line. All the subsequent descriptions of these insulated conductor or wiring lines are expressed as cable lines or just cables for convenience unless explicitly expressed otherwise. The dc power controller 2 may be placed between the dc electrical source 1 and the electrode 7. It may also be placed in cable line 102 to connect with the dc electrical source 1. It may also be placed between the cable line 101 and cable line 102 as shown in the FIG. 1. Generally, the dc power controller 2 may be placed anywhere in the dc circuit so long as it can effectively and efficiently control the voltage and/or current whenever it is needed or desirable. Similarly, the RF isolation transformer 3 may also be placed anywhere in the dc circuit even though FIG. 1 shows it is placed between the dc power controller 2 through cable 103 and the electrode 9 through cables 104 and 107. Consequently, FIG. 1 illustrates a dc circuit comprising the dc electrical source 1, the dc power controller 2, the RF isolation transformer 3, the first electrode 9, the second electrode 7, and cables 101, 102, 103, 104 and 107 as the functional portion of the dc circuit to perform smoke particle ionization and removal or reduction of the ionized smoke particles generated at a surgical site. It will be understood that the dc circuit may also contain as many switches or controls as necessary to control or monitor the dc circuit during a surgical operation.

The high voltage dc electrical source 1 in accordance with FIG. 1 may be from a mains power supply for the generation of the high voltage necessary for ionization of smoke particles. But it may be replaced or supplemented by a rechargeable storage battery. The high voltage dc electrical source 1 may be constant or interrupted by a switch operable by a surgeon or his/her assistant, for example a thumb operated switch or a foot pedal, to provide manual control (not shown in FIG. 1).

The dc power controller 2 is included to control or monitor the current or voltage in the dc circuit. It will, for example, stop the current flow very quickly should the current increase rapidly in a short span of time. This will avoid or reduce accidental voltage shocks to the subject under a surgical procedure or operation. Additionally, it is possible to monitor increased impedance, and thereby detect a blocked electron emission. The dc power controller can be placed anywhere in the dc circuit as indicated above.

The RE isolation transformer 3 is incorporated into the circuit to make sure any RF current is eliminated during the dc ionization process to safeguard the safety of the subject under the surgical procedure or operation. It can be placed anywhere in the dc circuit as indicated above. Preferably, it may be placed close to the dc electrical source. The RF isolation transformer may be selected from those commercially available such as Jensen transformers, Kramer transformers and others. A selection of a dc power controller or a RF isolation transformer should be well within the ambit of a person of ordinary skill in the art.

When connected, for example, through a plug-socket mechanism, to the negative pole of the high voltage dc electrical source 1, the electrode 9 serves as the ionizing power to negatively charge the particles generated at or around a surgical site. In keeping with accepted theory, it sends a stream of electrons toward the atoms of the smoke particles causing the atoms to form negative ions and thereby becoming attracted to the positively charged electrode 7. Under this situation, the electrode 9 may be made with a sharp tip or may include a shield and a tip such as disclosed in the US application publication No. 2012/0,067,212. The electrode 9 may also be made to include a positively charged accelerator ring. The accelerator ring improves the performance of the electrode 9 by drawing ions in the direction of their intended flow, in this case towards the electrode 7. The electrode 9 may further be made to have a conductive rod having a tip and a shield. The shield may terminate in a coiled spring-like formation covering the tip and protecting the subject from unintended trauma caused by the tip when in use. In one version the spring is not conductive and acts solely as a shield for said protection which can retract on insertion to expose the tip, whereas in another version the spring may be conductive to improve the performance of the electrode in producing electrons, but need not be retractable to expose the tip. In this latter configuration, it is the coiled formation that releases the electrons to form ions as disclosed in the US application publication No. 2012/0,067,212.

As described above when the electrode 9 is connected to the negative pole of the high voltage dc electrical source, the electrode 7 is then connected to the positive pole of the high voltage dc electrical source to serve as a smoke particle collecting patch. The electrode 7 should accordingly be made to have a large surface area to facilitate collection of the negatively charged particles. The electrode 7 may also be made to increase its surface area through disposition over other electrodes in the RF circuit such as electrode 8 and electrode 10 which will be discussed in later paragraphs. It will be understood that insulating materials are needed to separate these electrodes to prevent them from interfering with each other. Methods of placing or mounting one electrode over another electrode are well known in the art, for example, as disclosed in U.S. Pat. Nos. 3,970,088 and 6,942,662.

The electrode 7 may be configured to be connectable with the dc electrical source 1 similarly through a plug/socket mechanism. For example, a plug may be extended from the dc source 1 through an insulated cable line to the electrode 7. Alternatively, a plug may be extended from the electrode 7 through an insulated cable line to connect with the dc source 1.

The RF circuit in accordance with FIG. 1 includes a surgical radio frequency energy generator 5, a third electrode 8, a fourth electrode 10, and a switch 4. The RF circuit in accordance with FIG. 1 may also include the first electrode 9 of the dc circuit described above and configured to be connectable to the RF circuit through the switch 4. Further included in the RF circuit is a RF current and voltage controller (not shown) which may be placed any place in the RF circuit. The third electrode 8 is configured to be connectable to the RF generator 5 through the switch 4 by cables 105 and 106. The fourth electrode 10 is configured to be connectable to the RF generator 5 through cable 108. Accordingly, FIG. 1 illustrates a RF circuit comprising the surgical RF generator 5, a RF controller (not shown), the switch 4, the electrode 8, the electrode 9, the electrode 10, and cables 105, 106, 107 and 108 as the functional portion of the RF circuit to perform a surgical procedure or operation on a subject.

The surgical RF energy generator 5 should have a frequency of between 100 KHz and 100 MHz. More preferable, the frequency should be between 300 kHz and 2 MHz. This type of surgical RF energy generator is well understood by a person skilled in the art either for tissue cutting, cauterization, sealing or coagulation. The RF controller is included to monitor and/or control the RF output for different purposes such as cutting, coagulation or sealing. Additional RF controllers may also be included in the RF circuit to control or monitor the RF circuit to guarantee the safety of the subject under a surgical procedure or operation. This type of RF controller is also well understood and known by a skilled person in the art.

The switch 4 in accordance with FIG. 1 may be in the form of knobs, touches, slides, push buttons, magnetic or even remote type of controls, which are all within the grasp of a skilled person in the art. It may also be in the form of a computer or a computerized tool. The switch 4 in the RE circuit may, for example, be designed in a manner as disclosed in the U.S. Pat. Nos. 5,472,442, 5,312,327 and PCT application publication No. WO2014/151,560.

In accordance with FIG. 1, both the electrodes 8 and 10 are configured to be capable of performing tissue coagulation or sealing. Consequently, these two electrodes may be made to possess larger surface area in comparison with the electrode 9 which should be made to possess small surface area since it is configured to be used as a cutting blade in the RF circuit. Additionally, a connecting point 12 is configured to connect the electrode 9 into the RF circuit through the switch 4 through cable 107. Cable 104 may be lumped into cable 107 to form a single cable line for easy manipulation. It should be understood that the design of this type of cable connections is well known by a skilled person in the art.

As shown in FIG. 1 when connected to the surgical RF energy generator 5 through the switch 4, the electrode 8 may form a bipolar sealing or coagulating device with the electrode 10. Therefore, the dc circuit may be turned on to remove or reduce the smoke particles when the RF circuit is switched on to perform tissue sealing or coagulation at a surgical site of a subject. When connected to the surgical RF energy generator 5 through the switch 4, the electrode 9 may be used as a cutting blade and the electrode 10 may be used as a return current pad in the RF circuit. Consequently, the dc circuit may be turned on to remove or reduce the smoke particles when the RF circuit is switched on to perform tissue cutting at a surgical site of a subject. The electrode 9 may be configured to be connectable to the RF circuit through the switch 4. The electrode 9 may be switched on or off the RF circuit through the switch 4 depending on the need of the situation. The switch 4 may be configured to enable the electrode 9 to perform tissue cutting and to enable the electrodes 8 and 10 to perform tissue sealing or coagulation at the same time. Consequently, the dc circuit may be turned on to remove or reduce the smoke particles when the RF circuit is switched on to perform tissue cutting and coagulation at a surgical site of a subject. The dc circuit may be turned on simultaneously, concurrently, alternatively, intermittently, or sequentially when the RF circuit is switched on to perform the tissue cutting and/or coagulation. The materials and methods suitable for making the electrodes 8, 9 and 10 are well understood in the art for tissue cutting, sealing or coagulation, for example as disclosed U.S. Pat. Nos. 4,862,890, 4,958,539, 8,357,155, and 8,852,183.

Consequently, a device or system in accordance with FIG. 1 may be used as a bipolar cutting device, and/or a bipolar sealing or coagulating device in addition to being used as a smoke particle extractor. It is contemplated that the device or system may perform tissue cutting and/or coagulation and smoke extraction simultaneously, concurrently, alternatively, intermittently, or sequentially.

Further in accordance with FIG. 1, the block 11 containing the electrodes 7, 8, 9 and 10 may be configured to form an insertable front portion of the device or system. Selections of size and/or dimension and/or material of the electrodes 7, 8, 9, and 10 each for their respective roles as cutting, sealing or coagulating, ionizing, or particle collecting are within the grasp of a killed person in the art. For example, the electrode 9 should be made narrow and sharp if it is to be used as a cutting blade in the RF circuit so that it can have high current density for an efficient cut, and it will also serve its purpose to be used as an ionizing source in the dc circuit. As for the electrode 7, on the contrary, it is to be made to possess a large surface area if it is to be used to attract and collect negatively charged particles. The electrode 7 or the electrode 9 may be configured to be connectable to the dc electricity source through a separate plug/socket system. Or, they may be bundled together by cables 101, 104, and 107 to form an integrated plug/socket system to connect with the dc circuit. The block 11 may also include switch 4 in the handle portion of the device for easy and convenient operation by the operator.

In accordance with FIG. 1, the block 6 containing the dc power source 1 and the RF power source 5 may form separate parts configured to be connectable with the block 11 through a plug/socket system or other means that are well understood by a skilled person in the art. The plug/socket system may also include additional hand switches and/or foot pedals whenever desired or necessary.

When a device or system in accordance with FIG. 1 is put into use, the following steps are contemplated: connecting the electrodes 7 and 9 with the dc electrical source 1 properly; checking to make sure the dc power controller 2, the RF isolation transformer 3 and any other switches and/or controls in the dc circuit are all in good and safe working conditions; properly connecting the switch 4 to the electrode 9 when performing tissue cutting; checking to make sure the RF controller and any other switches and/or controls in the RF circuit are all in good and safe working conditions; inserting the block 11 portion into its intended place where a surgical procedure or operation is desired; and then properly switching on the RF circuit to perform tissue cutting and/or tissue sealing and properly switching on the dc circuit to ionize and to collect smoke particles generated at a surgical site. Similarly, properly connecting the electrodes 8 and 10 through the switch 4 when performing tissue sealing or coagulation is desired. Likewise, properly connecting the electrodes 8, 9, and 10 through the switch 4 when both performing tissue cutting and performing tissue sealing or coagulation are desired. These steps may be repeated as many times as necessary. The dc circuit and the RF circuit may be switched on simultaneously, concurrently, alternatively, intermittently, or sequentially.

Figure 2:
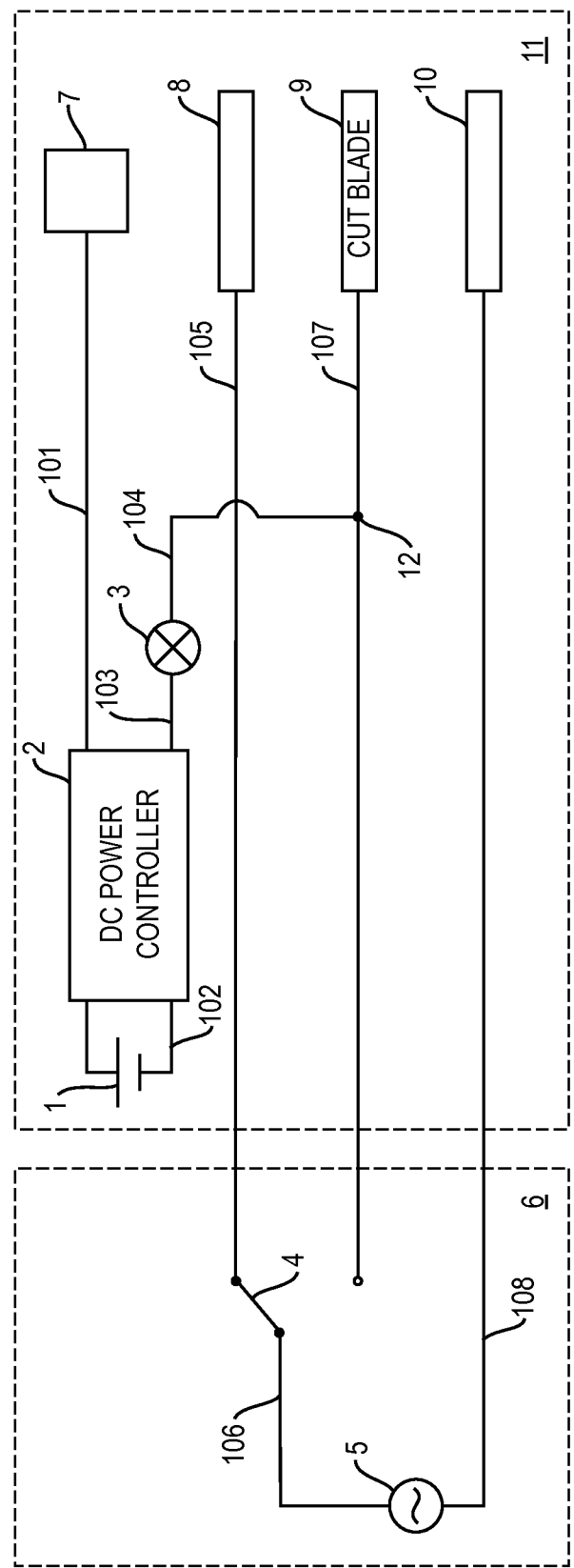
FIG. 2 is a schematic representation of a device or system in accordance with one embodiment of the present disclosure wherein the source of the high voltage dc electricity is disposed with the electrodes in the same block, and additionally, the ionizing electrode in the dc circuit is also configured to be used as a cutting electrode in the RF circuit.

FIG. 2 shows a variation of a device or system in accordance with one aspect of the present disclosure. The device or system in accordance with FIG. 2 shares substantial similarities with a device or system of FIG. 1 except that the high voltage dc source 1 is configured to be disposed in the block 11 where all the electrodes are disposed. In this embodiment, the dc power source 1, for example, may be provided by a battery pack. The battery pack may be detachable from the device and may be rechargeable. The dc power source 1 may be disposed in the handle portion of the device. The electrodes 7, 8, 9 and 10 may be configured to be disposed in the front portion of the device. The electrodes 7, 8, 9 and 10 may be configured to form the insertable portion of the device or system. The device or system in accordance with FIG. 2 may be used in substantially similar ways as described above for FIG. 1 such as for bipolar cutting and/or bipolar tissue sealing or coagulation. A device in accordance with FIG. 2 may be made portable such that all the electrodes are disposed in the front portion of the device and the dc power source is disposed in the handle portion. The device or system in accordance with FIG. 2 may be connectable with a surgical RE generator through a plug/socket system or other means well known in the art.

Figure 3:
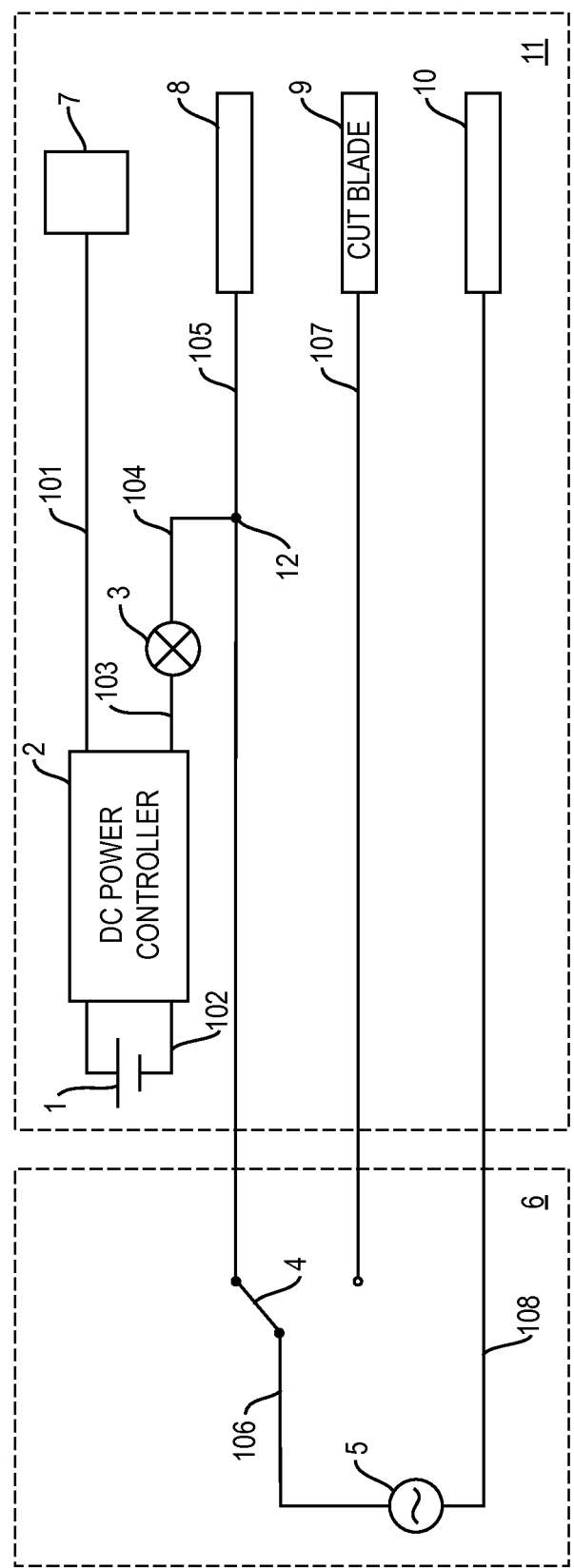
FIG. 3 is a schematic representation of a device or system in accordance with one embodiment of the present disclosure wherein the source of the high voltage dc electricity is disposed with the electrodes in the same block, and additionally, one electrode in the dc circuit is also configured to be used as a switchable sealing electrode in the RF circuit.

FIG. 3 shows another variation of a device or system in accordance with one aspect of the present disclosure. A device or system in accordance with FIG. 3 shares many similarities with a device of FIG. 1 or FIG. 2. The significant difference comes from the fact that one of the two sealing or coagulating electrodes is incorporated into the dc circuit instead of the cutting blade as in FIG. 1 or FIG. 2. Additionally, the sealing electrode can be switched off the dc circuit through the switch 4. When that happens, the cutting electrode 9 and the other sealing electrode 10 may form a tissue cutting device in the RF circuit to cut tissues when connected to the surgical RE generator 5. When connected with the surgical RF energy source 5 through the switch 4 as shown in FIG. 3, the electrode 8 may form a bipolar sealing or coagulation device with the electrode 10 to perform tissue sealing or coagulation. Consequently, a device of FIG. 3 may be used as a bipolar cutting device or a bipolar sealing device substantially similar to a device of FIG. 1 or FIG. 2. Also similar to a device or system of FIG. 2 in that the high voltage dc source 1 is disposed in the same block 11 as all the electrodes, the dc power source 1 may accordingly be provided by a battery pack. The battery pack may be detachable from the device and may be rechargeable. The dc power source may be configured to be in the handle portion of the device. The electrodes 7, 8, 9 and 10 may be configured to be disposed in the front portion of the device. The electrodes 7, 8, 9 and 10 may be configured to form the insertable portion of the device.

Figure 4:
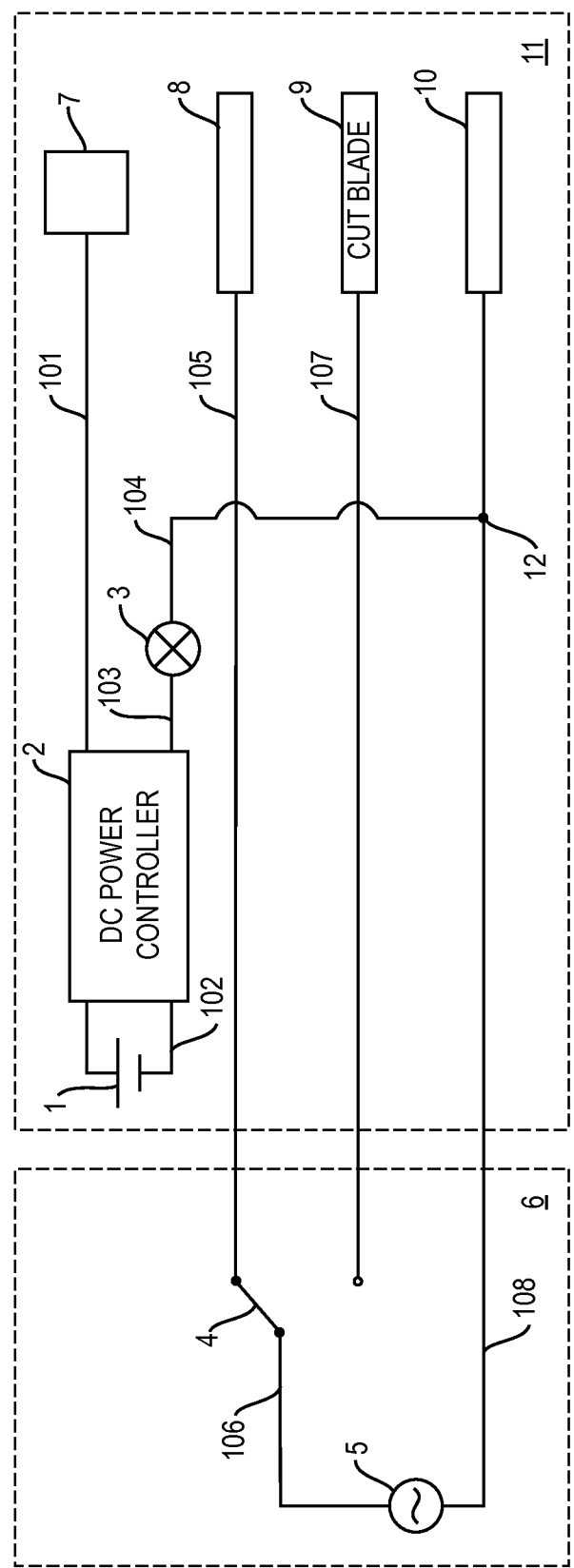
FIG. 4 is a schematic representation of a device or system in accordance with one embodiment of the present disclosure wherein the source of the high voltage dc electricity is disposed with the electrodes in the same block, and additionally, one electrode in the dc circuit is also configured to be used as a non-switchable sealing electrode in the RF circuit.

FIG. 4 shows another variation of a device or system in accordance with one aspect of the present disclosure. A device in accordance with FIG. 4 shares many similarities with a device of FIG. 3. In particular, both the device of FIG. 4 and the device of FIG. 3 use one of the two RF sealing or coagulating electrodes in the dc circuit. A device or system in accordance with FIG. 4, however, is configured to incorporate the non-switchable sealing electrode 10 into the dc circuit, meaning the electrode cannot be switched off the dc circuit by the switch 4. Instead, it is a fixed part of the RF circuit. Consequently, when connected with the electrode 8 through the switch 4, the electrode 10 may form a bipolar tissue sealing or coagulation device in the RF circuit. Yet when connected with the electrode 9 through the switch 4, the electrode 10 may form a bipolar tissue cutting device in the RF circuit. As a result, a device or system of FIG. 4 may be used as a bipolar cutting device or a bipolar sealing device substantially similar to a device of FIG. 1, FIG. 2, or FIG. 3. Also similar to a device or system of FIG. 2 or FIG. 3 in that the high voltage dc source 1 is disposed in the same block 11 as the electrodes 7, 8, 9 and 10, the dc power source 1 may accordingly be provided by a battery pack. The battery pack may be detachable from the device and may be rechargeable. The dc power source may be configured to be disposed in the handle portion of the device. The electrodes 7, 8, 9 and 10 may be configured to be disposed in the front portion of the device. A device in accordance with FIG. 4 may be similarly operable as a device of FIG. 1, FIG. 2, or FIG. 3.

Figure 5:
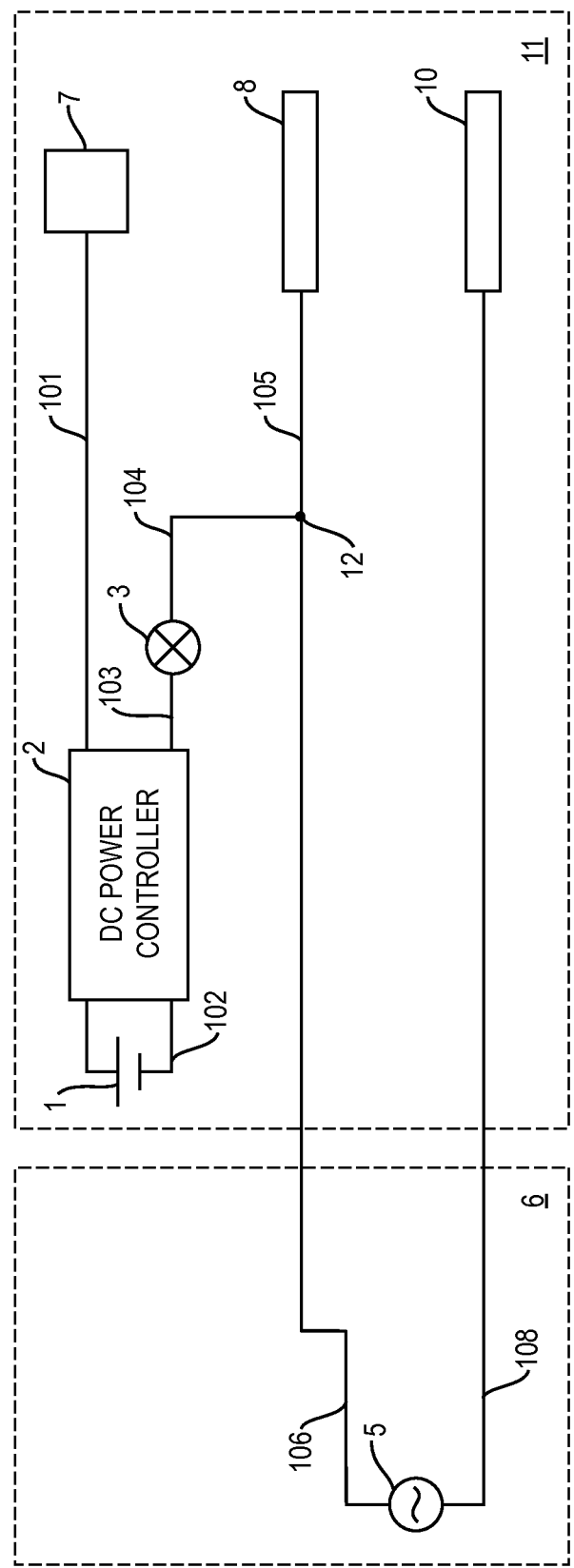
FIG. 5 is a schematic representation of a device or system in accordance with one embodiment of the present disclosure wherein the source of the high voltage dc electricity is disposed with the electrodes in the same block, and additionally, one electrode in the dc circuit is also configured to be used as a non-switchable sealing electrode in the RF circuit.

FIG. 5 shows another variation of a device in accordance with one aspect of the present disclosure. The device contains a dc circuit and a RF circuit. The dc circuit includes a high voltage dc electrical source 1, a dc power controller 2, a RF isolation transformer 3, a first electrode 8, and a second electrode 7. The electrode 7 is configured to be connectable to the high voltage dc electrical source 1 through an insulated conductor or wiring line 101. As previously described, the dc power controller 2 may be placed anywhere in the dc circuit so long as it can effectively and efficiently control the voltage and/or current whenever it is needed or desirable. Similarly, the RE isolation transformer 3 may also be placed anywhere in the dc circuit even though FIG. 5 shows it is placed between the dc power controller 2 through cable 103 and the electrode 8 through cables 104 and 105. Consequently, FIG. 5 illustrates a dc circuit comprising the dc electrical source 1, the dc power controller 2, the RF isolation transformer 3, the first electrode 8, the second electrode 7, and cables 101, 102, 103, 104 and 105 as the functional portion of the dc circuit to perform smoke particle ionization and removal or reduction of the ionized smoke particles generated at a surgical site. It will be understood that the dc circuit of FIG. 7 performs smoke particle reduction or removal in ways similar to what was previously described for FIG. 1. It will also be understood that the dc circuit may contain as many switches or controls as necessary to control or monitor the dc circuit.

The RE circuit in accordance with FIG. 5 includes a surgical radio frequency energy generator 5, the electrode 8, and a third electrode 10. As a result, the electrode 8 is included both in the dc circuit and in the RF circuit. Also included in the RF circuit is at least a RF current and voltage controller (not shown) which may be placed any place in the RF circuit. The third electrode 10 is connected to the surgical RF generator 5 through cable 108. The electrode 8 is connected to the surgical RF generator 5 through cables 105 and 106. Accordingly, FIG. 5 illustrates a RF circuit comprising the RF generator 5, a RF controller (not shown), the electrode 8, the electrode 10, and cables 105, 106, and 108 as the functional portion of the RF circuit to perform a surgical procedure or operation on a subject.

As shown in FIG. 5, when connected to the RF surgical RF energy generator 5 through cables 105 and 106, the electrode 8 may form a bipolar sealing or coagulating device with the electrode 10. Therefore, the dc circuit may be turned on to remove or reduce the smoke particles when the RF circuit is switched on to perform tissue sealing or coagulation at a surgical site of a subject. The dc circuit may be turned on simultaneously, concurrently, alternatively, intermittently, or sequentially when the RF circuit is switched on to perform the tissue sealing or coagulation.

In accordance with FIG. 5, the block 11 containing the electrodes 7, 8, and 10 may be configured to form an insertable front portion of the device or system. Selections of size and/or dimension and/or material of the electrodes 7, 8, and 10 each for their respective roles as sealing or coagulating, ionizing, or collecting are within the grasp of a killed person in the art. For example, the electrode 7 should be made narrow and sharp if it is to be used as an ionizing source in the dc circuit. As for the electrode 8, on the contrary, it is to be made to possess a large surface area if it is to be used to attract and collect negatively charged particles. The electrode 7 or the electrode 8 may be configured to be connectable to the dc electricity source through a separate plug/socket system. Or, they may be bundled together by cables 101 and 104 and 105 to form an integrated plug/socket system to connect with the dc circuit. Moreover, since the high voltage dc electrical source 1 shares the same block with the electrodes 7, 8, and 10, the dc electrical source 1, for example, may be provided by a battery pack. The battery pack may be detachable from the device and may be rechargeable. The dc electrical source 1 may be configured to be disposed in the handle portion of the device. The electrodes 7, 8, and 10 may be configured to be disposed in the front portion of the device.

Figure 6:
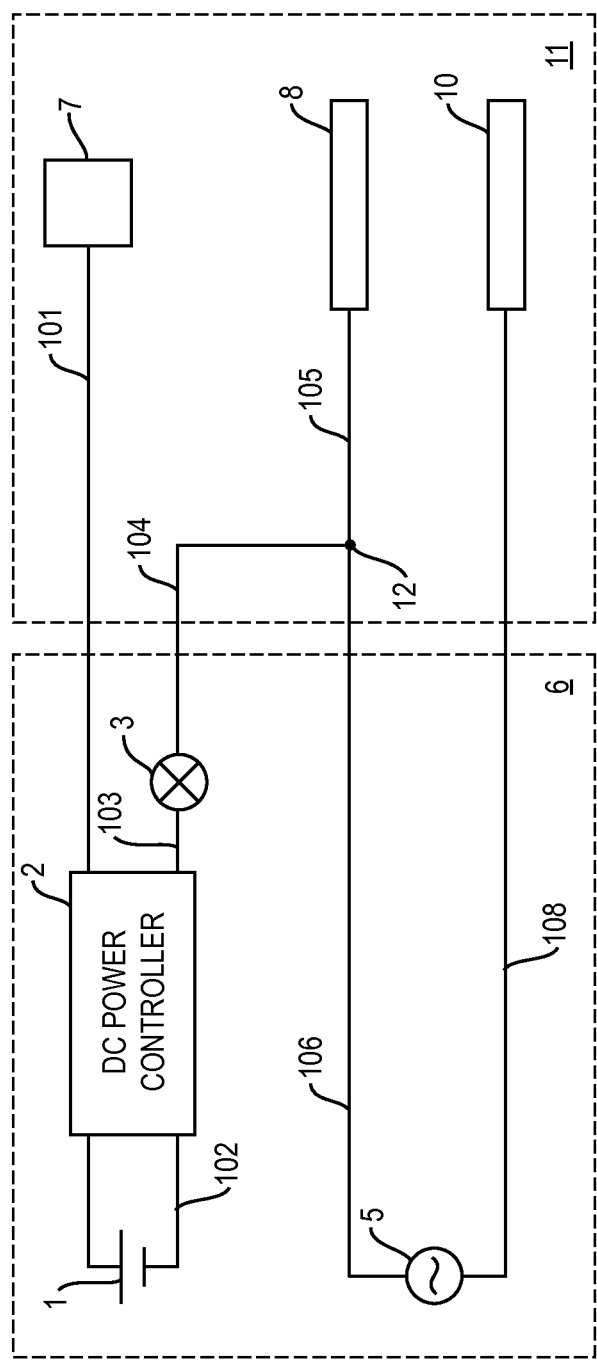
FIG. 6 is a schematic representation of a device or system in accordance with one embodiment of the present disclosure wherein the source of the high voltage dc electricity is disposed separately from the electrodes, and additionally, one electrode in the dc circuit is also configured to be used as a non-switchable sealing electrode in the RF circuit.

FIG. 6 shows another variation of a device in accordance with one aspect of present disclosure. The device in accordance with FIG. 6 shares substantial similarities with a device of FIG. 5 except that the high voltage dc source 1 of FIG. 6 is separately disposed in the block 6 instead of the block 11. As a result, the connection of the block 11 containing the electrodes 7 and 8 in the dc circuit with the block 6 containing the dc electrical source 1 may be through a plug/socket mechanism, or through some other mechanisms known in the art. Also, the block 11 containing the electrodes 7, 8, and 10 may be configured to be disposed in the front portion of the device. The electrodes 7, 8, and 10 may be configured to form an insertable portion of the device. A device in accordance with FIG. 6 may be made portable such that all the electrodes are disposed in the front portion of the device and that it is connectable with a RF generator through a plug/socket system or other means well known in the art.

The device or system in accordance with FIG. 6 may be used in substantially similar ways as described for a device of FIG. 5. It may be particularly suitable for removing or reducing smoke particles generated during bipolar tissue sealing or coagulation by the device.

Figure 7:
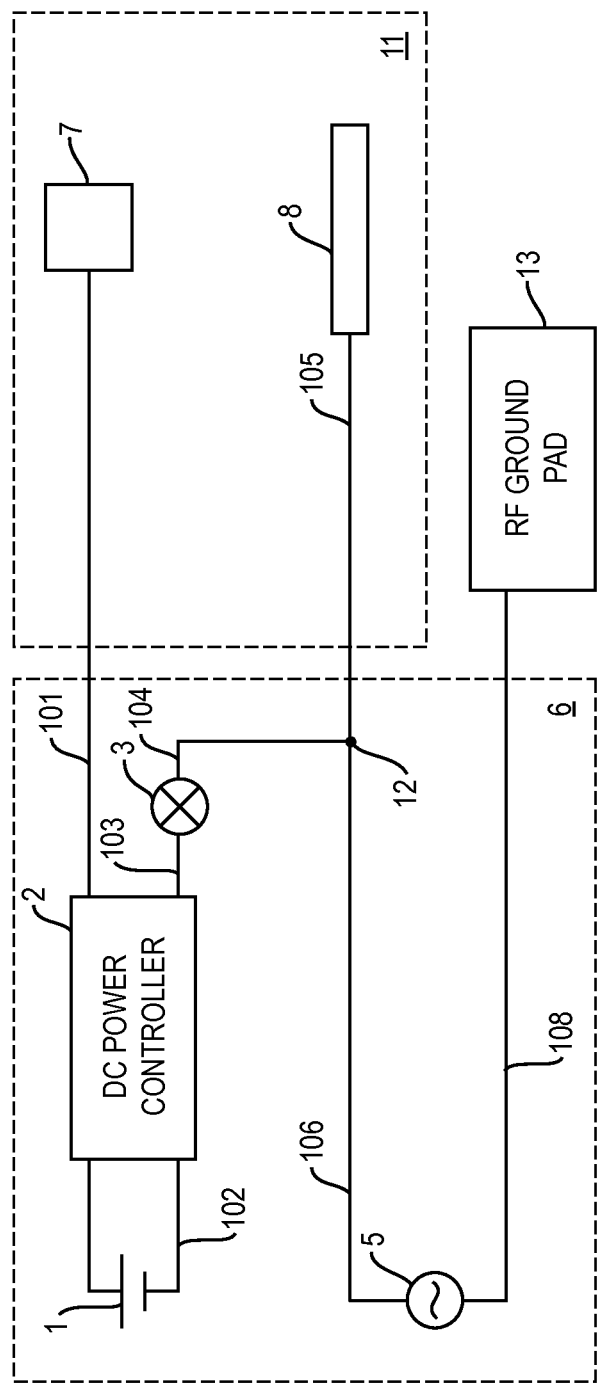
FIG. 7 is a schematic representation of a device or system in accordance with one embodiment of the present disclosure wherein the source of the high voltage dc electricity is disposed separately from the electrodes, and additionally, one electrode in the dc circuit is also configured to be used as the cutting electrode in the RF circuit.

FIG. 7 shows another variation of a device or system in accordance with one aspect of the present disclosure. The device contains a dc circuit and a RF circuit. The dc circuit includes a high voltage dc electrical source 1, a dc power controller 2, a RF isolation transformer 3, a first electrode 8, and a second electrode 7. The electrode 7 is connected to the high voltage dc electrical source 1 through an insulated conductor or wiring line 101. As described previously, the dc power controller 2 may be placed anywhere in the dc circuit so long as it can effectively and efficiently control the voltage and/or current whenever it is needed or desirable. Similarly, the RF isolation transformer 3 may also be placed anywhere in the dc circuit even though FIG. 7 shows it is placed between the dc power controller 2 through cable 103 and the electrode 8 through cables 104 and 105. Consequently, FIG. 7 illustrates a dc circuit comprising the dc electrical source 1, the dc power controller 2, the RF isolation transformer 3, the first electrode 8, the second electrode 7, and cables 101, 102, 103, 104 and 105 as the functional portion of the dc circuit to perform smoke particle ionization and removal or reduction of the ionized smoke particles generated at a surgical site. It will be understood that the dc circuit of FIG. 7 performs smoke particle reduction or removal in ways similar to what was previously described for FIG. 1. It will also be understood that the dc circuit may contain as many switches and/or controls as necessary to control or monitor the dc circuit.

The RE circuit in accordance with FIG. 7 includes a surgical radio frequency energy generator 5, a RF current return pad 13, and the electrode 8. As a result, the electrode 8 is incorporated into both the dc circuit and the RF circuit as well. Also included in the RE circuit is a RE current and voltage controller (not shown) which may be placed any place in the RE circuit. Accordingly, FIG. 7 illustrates a RF circuit comprising the RF generator 5, a RF controller (not shown), the electrode 8, the RF current return pad 13, and cables 105, 106, and 108 as the functional portion of the RF circuit to perform a surgical procedure or operation on a subject.

As shown in FIG. 7, when connected to the RF surgical RF energy generator 5 through cables 105 and 106, the electrode 8 may form a monopolar cutting device with the RF current return pad 13. Therefore, the dc circuit may be turned on to remove or reduce the smoke particles when the RF circuit is switched on to perform tissue cutting at a surgical site of a subject. The dc circuit may be turned on simultaneously, concurrently, alternatively, intermittently, or sequentially when the RF circuit is switched on to perform the tissue cutting.

Figure 8:
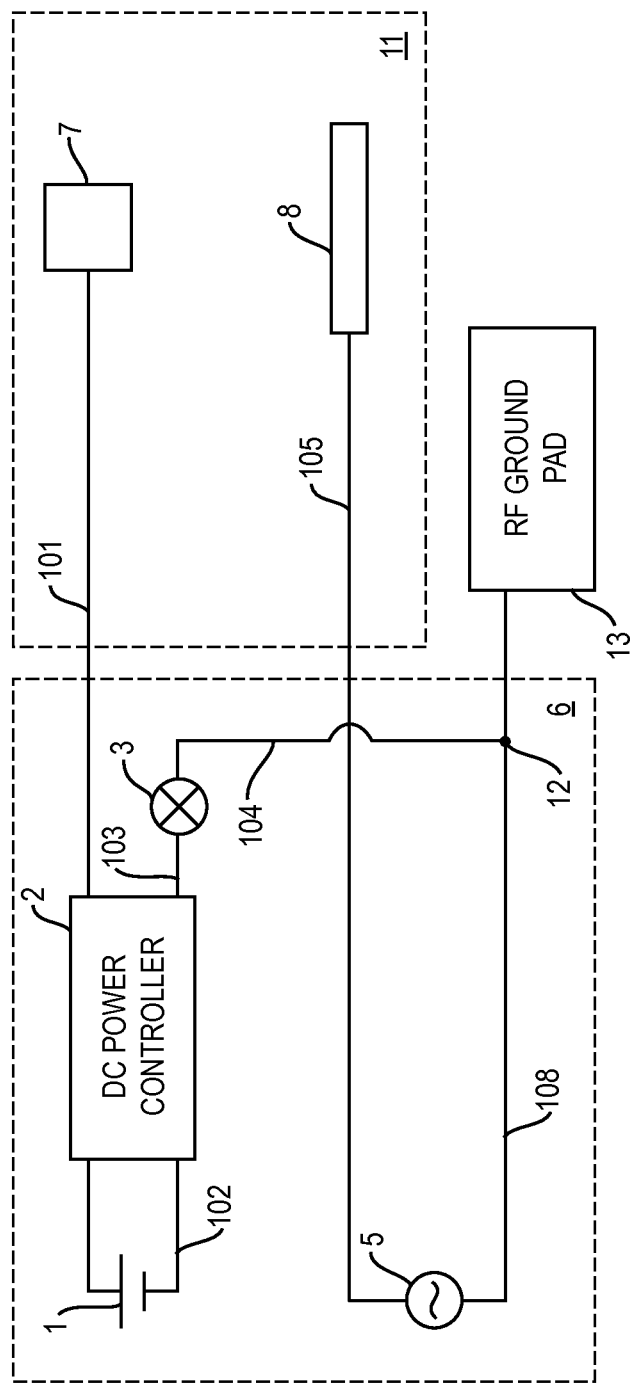
FIG. 8 is a schematic representation of a device or system in accordance with one embodiment of the present disclosure wherein the source of the high voltage dc electricity is disposed separately from the electrodes, and additionally, the particle collecting patch in the dc circuit is also configured to be used as the ground pad electrode in the RF circuit.

FIG. 8 shows another variation of a device or system in accordance with one aspect of the present disclosure. The device contains a dc circuit and a RF circuit. The dc circuit includes a high voltage dc electrical source 1, a dc power controller 2, a RF isolation transformer 3, a first electrode 7, and a second electrode 13. The electrode 7 is configured to be connectable to the high voltage dc electrical source 1 through an insulated conductor or wiring line 101. As described previously, the dc power controller 2 may be placed anywhere in the dc circuit so long as it can effectively and efficiently control the voltage and/or current whenever it is needed or desirable. Similarly, the RF isolation transformer 3 may also be placed anywhere in the do circuit even though FIG. 8 shows it is placed between the dc power controller 2 through cable 103 and the electrode 13 through cable 104. Consequently, FIG. 8 illustrates a dc circuit comprising the dc electrical source 1, the dc power controller 2, the RE isolation transformer 3, the first electrode 7, the second electrode 13, and cables 101, 102, 103, and 104 as the functional portion of the dc circuit to perform smoke particle ionization and removal or reduction of the ionized smoke particles generated at a surgical site. It will be understood that the dc circuit of FIG. 8 performs smoke particle reduction or removal in ways similar to what was previously described for FIG. 1. It will also be understood that the dc circuit may contain as many switches or controls as necessary to control or monitor the dc circuit.

The RF circuit in accordance with FIG. 8 includes a radio frequency energy generator 5, a third electrode 8, and the electrode 13. As a result, the electrode 13 is configured to be included both in the dc circuit and in the RF circuit. More particularly, the electrode 13 in accordance with FIG. 8 is configured to be an ionized particle collecting patch in the dc circuit and a RE current return pad in the RF circuit. Also included in the RF circuit is a RF current and voltage controller (not shown) which may be placed any place in the RF circuit. Accordingly, FIG. 8 illustrates a RF circuit comprising the RF generator 5, a RE controller (not shown), the electrode 8, the RF current return pad 13, and cables 105, and 108 as the functional portion of the RF circuit to perform a surgical procedure or operation on a subject.

As shown in FIG. 8, when connected to the RF surgical RF energy generator 5 through cable 105, the electrode 8 may form a monopolar cutting device with the RF current return pad 13. Therefore, the dc circuit may be turned on to remove or reduce the smoke particles when the RF circuit is switched on to perform tissue cutting at a surgical site of a subject. The dc circuit may be turned on simultaneously, concurrently, alternatively, intermittently, or sequentially when the RF circuit is switched on to perform the tissue cutting.

Figure 9:
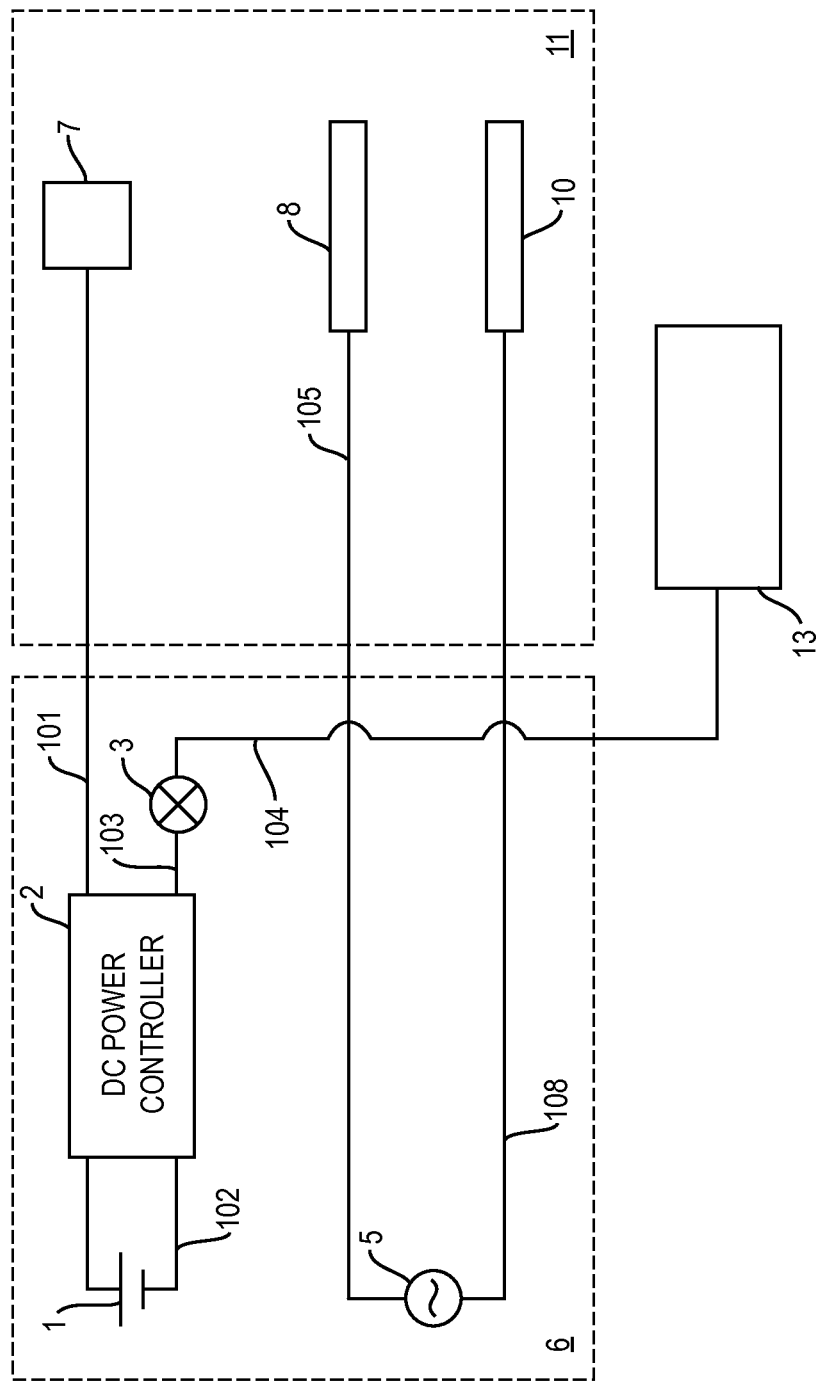
FIG. 9 is a schematic representation of a device or system in accordance with one embodiment of the present disclosure wherein the source of the high voltage dc electricity is disposed separately from the electrodes, and additionally, the particle collecting patch electrode in the dc circuit is configured to be movable or external.

FIG. 9 shows another variation of a device or system in accordance with one aspect of the present disclosure. The device contains a dc circuit and a RF circuit. The dc circuit of FIG. 9 includes a high voltage dc electrical source 1, a dc power controller 2, a RF isolation transformer 3, a first electrode 7, and a second electrode 13. The electrode 7 is configured to be connectable to the high voltage dc electrical source 1 through an insulated conductor or wiring line 101. As described previously, the dc power controller 2 may be placed anywhere in the dc circuit so long as it can effectively and efficiently control the voltage and/or current whenever it is needed or desirable. Similarly, the RE isolation transformer 3 may also be placed anywhere in the dc circuit even though FIG. 9 shows it is placed between the dc power controller 2 through cable 103 and the electrode 13 through cable 104. Consequently, FIG. 9 illustrates a dc circuit comprising the dc electrical source 1, the dc power controller 2, the RF isolation transformer 3, the first electrode 7, the second electrode 13, and cables 101, 102, 103 and 104 as the functional portion of the dc circuit to perform smoke particle ionization and removal or reduction of the ionized smoke particles generated at a surgical site. It will be understood that the dc circuit of FIG. 9 performs smoke particle reduction or removal in ways similar to what was previously described for FIG. 1. It will also be understood that the dc circuit may contain as many switches or controls as necessary to control or monitor the dc circuit.

The RF circuit in accordance with FIG. 9 includes a radio frequency energy generator 5, a third electrode 8, and a fourth electrode 10. Also included in the RF circuit is a RF current and voltage controller (not shown) which may be placed any place in the RF circuit. Accordingly, FIG. 9 illustrates a RF circuit comprising the RF generator 5, a RF controller (not shown), the electrode 8, the electrode 10, and cables 105 and 108 as the functional portion of the RF circuit to perform a surgical procedure or operation on a subject.

As shown in FIG. 9, when connected to the surgical RF energy generator 5 through cable 105, the electrode 8 may form a bipolar tissue sealing or coagulation device with the electrode 10. Therefore, the dc circuit may be turned on to remove or reduce the smoke particles when the RF circuit is switched on to perform tissue sealing or coagulation at a surgical site of a subject. The dc circuit may be turned on simultaneously, concurrently, alternatively, intermittently, or sequentially when the RF circuit is switched on to perform the tissue sealing or coagulation.

In accordance with FIG. 9, the block 11 containing the electrodes 7, 8, and 10 may be configured to form an insertable front portion of the device or system. Selections of size and/or dimension and/or material of the electrodes 7, 8, and 10 each for their respective roles as sealing or coagulating, or ionizing are within the grasp of a skilled person in the art. For example, the electrode 7 should be similarly made as the electrode 9 of a device of FIG. 1 for the purpose as an ionizing electrode in the dc circuit. As for the electrode 13, on the contrary, it is to be made to possess a large surface area to attract and collect negatively charged particles.

In accordance with FIG. 9, the block 6 containing the dc power source 1 and the RE power source 5 may form separate parts configured to be connectable with the block 11 through a plug/socket system or other means that are well understood by a skilled person in the art. The plug/socket system may also include additional hand switches and/or foot pedals whenever desired or necessary.

Figure 10:
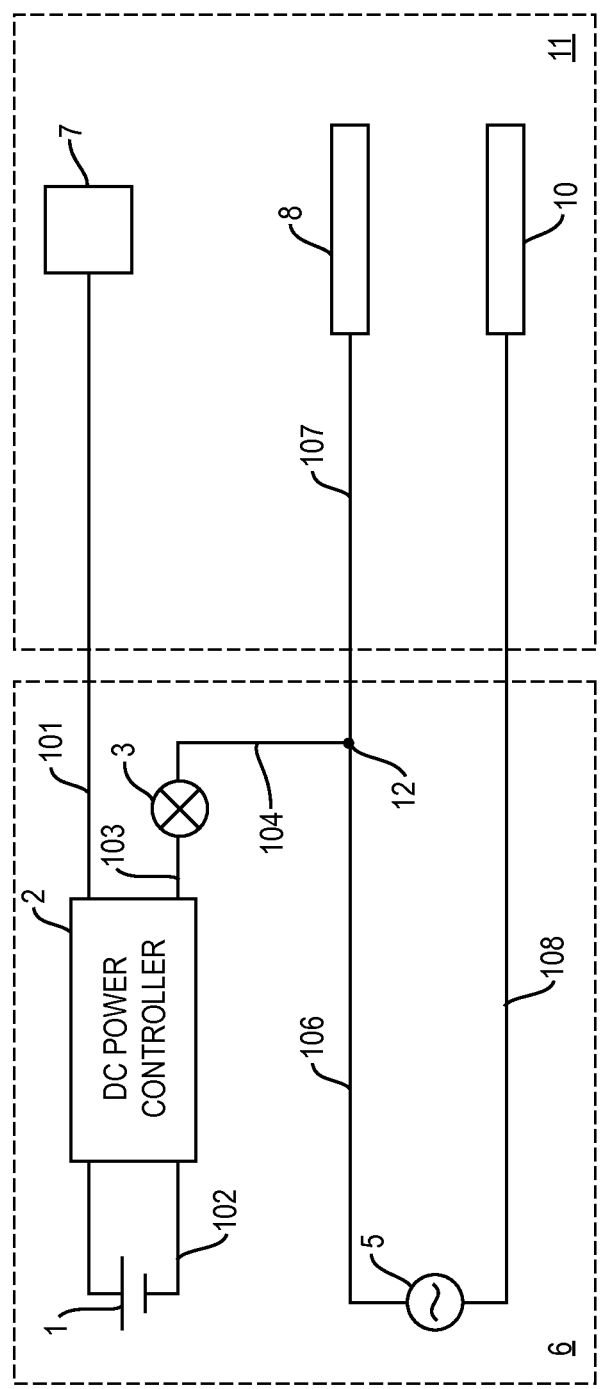
FIG. 10 is a schematic representation of a device or system in accordance with one embodiment of the present disclosure wherein the source of the high voltage dc electricity is disposed separately from the electrodes, and additionally, one electrode in the dc circuit is also configured to be used as a non-switchable sealing electrode in the RF circuit.

FIG. 10 shows another variation of a device or system in accordance with one aspect of the present disclosure. The device contains a dc circuit and a RF circuit. The dc circuit of FIG. 10 includes a high voltage dc electrical source 1, a dc power controller 2, a RF isolation transformer 3, a first electrode 7, and a second electrode 8. The electrode 7 is configured to be connectable to the high voltage dc electrical source 1 through an insulated conductor or wiring line 101. As previously described, the dc power controller 2 may be placed anywhere in the dc circuit so long as it can effectively and efficiently control the voltage and/or current whenever it is needed or desirable. Similarly, the RF isolation transformer 3 may also be placed anywhere in the dc circuit even though FIG. 10 shows it is placed between the dc power controller 2 through cable 103 and the electrode 8 through cables 104 and 107. Consequently, FIG. 10 illustrates a dc circuit comprising the dc electrical source 1, the dc power controller 2, the RF isolation transformer 3, the first electrode 7, the second electrode 8, and cables 101, 102, 103, 104, and 107 as the functional portion of the dc circuit to perform smoke particle ionization and removal or reduction of the ionized smoke particles generated at a surgical site. It will be understood that the dc circuit of FIG. 10 performs smoke particle reduction or removal in ways similar to what was previously described for FIG. 1. It will also be understood that the dc circuit may contain additional switches or controls as necessary to control or monitor the dc circuit.

The RF circuit in accordance with FIG. 10 includes a radio frequency energy generator 5, a third electrode 10, and the electrode 8. As a result, the electrode 8 is configured to be included both in the dc circuit and in the RF circuit. Further included in the RF circuit is a RE current and voltage controller (not shown) which may be placed any place in the RF circuit. Accordingly, FIG. 10 illustrates a RF circuit comprising the RE generator 5, a RF controller (not shown), the electrode 8, the electrode 10, and cables 106, 107 and 108 as the functional portion of the RF circuit to perform a surgical procedure or operation on a subject. It will be understood that the RF circuit may also contain additional switches or controls as necessary to control or monitor the RF circuit.

As shown in FIG. 10, when connected to the surgical RF energy generator 5 through cables 105 and 107, the electrode 8 may form a bipolar tissue sealing or coagulation device with the electrode 10. Therefore, the dc circuit may be turned on to remove or reduce the smoke particles when the RF circuit is switched on to perform tissue sealing or coagulation at a surgical site of a subject. The dc circuit may be turned on simultaneously, concurrently, alternatively, intermittently, or sequentially when the RF circuit is switched on to perform the tissue sealing or coagulation.

In accordance with FIG. 10, the block 11 containing the electrodes 7, 8, and 10 may be configured to form an insertable front portion of the device or system. Selections of size and/or dimension and/or material of the electrodes 7, 8, and 10 each for their respective roles as sealing or coagulating, ionizing, or particle collecting are within the grasp of a skilled person in the art. For example, the electrode 7 may be similarly made as the electrode 9 of a device of FIG. 1 if it is to be used as an ionizing electrode in the dc circuit. As for the electrode 8, on the contrary, it should be made to possess a large surface area if it is used to attract and collect negatively charged particles in the dc circuit.

In accordance with FIG. 10, the block 6 containing the dc power source 1 and the RF power source 5 may form separate parts configured to be connectable with the block 11 through a plug/socket system or other means that are well understood by a skilled person in the art. The plug/socket system may also include additional hand switches and/or foot pedals whenever desired or necessary.

It will be appreciated that when a device in accordance with FIG. 10 is put into use, the specific steps of using it are contemplated to be similar to those previously described, or may be easily adapted based on previous embodiments of the present disclosure.

Figure 11:
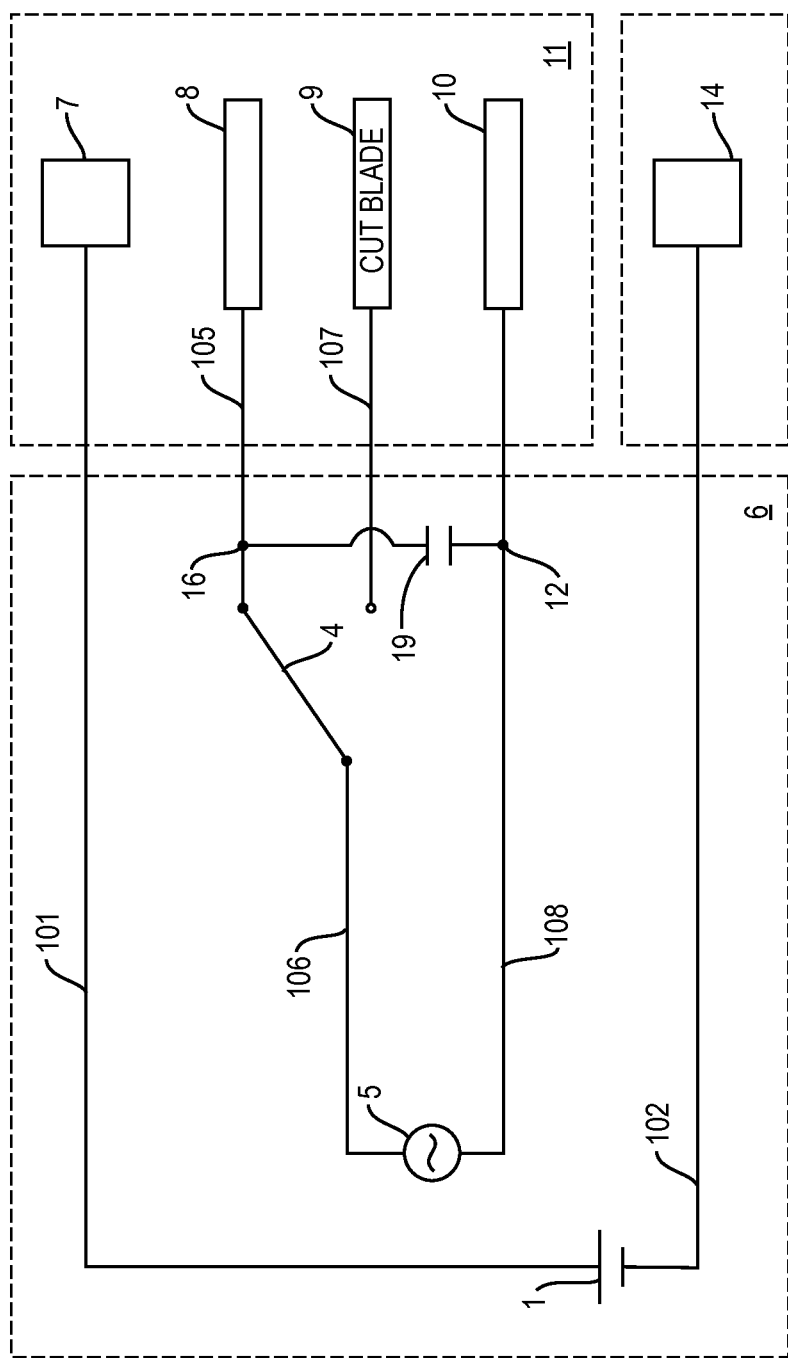
FIG. 11 is a schematic representation of a device or system in accordance with one embodiment of the present disclosure wherein the dc circuit and the RF circuit are independent and yet their respective electrodes are disposed in the same block.

FIG. 11 shows another variation of a device or system in accordance with one embodiment of the present disclosure. The device contains a dc circuit and a RF circuit. The dc circuit includes a high voltage dc electrical source 1, a dc power controller (not shown), a RF isolation transformer (not shown), a first electrode 7, and a second electrode 14. The electrode 7 is configured to be connectable to the high voltage dc electrical source 1 through an insulated conductor or wiring line 101. As previously described, the dc power controller may generally be placed anywhere in the dc circuit so long as it can effectively and efficiently control the voltage and/or current whenever it is needed or desirable. Similarly, the RF isolation transformer may also be placed anywhere in the dc circuit. Consequently, FIG. 11 illustrates a dc circuit comprising the dc electrical source 1, the first electrode 7, the second electrode 14, and cables 101 and 102 as the functional portion of the dc circuit to perform smoke particle ionization and removal or reduction of the ionized smoke particles generated at a surgical site. It will be understood that the dc circuit of FIG. 11 performs smoke particle reduction or removal in ways similar to what was previously described for FIG. 1. It will also be understood that the dc circuit may contain as many additional switches or controls as necessary to control or monitor the dc circuit.

The RE circuit in accordance with FIG. 11 includes a radio frequency energy generator 5, a third electrode 8, a fourth electrode 9, a fifth electrode 10, and a switch 4. Also included in the RF circuit is a capacitor 19 between the electrode 8 and the electrode 10. The capacitor allows the energy to go through to the electrode tips depending on the output of the capacitor. The function of this capacitor is well understood in the art. Further included in the RF circuit is a RF current and voltage controller (not shown) which may be placed any place in the RE circuit. The electrode 8 is configured to be connectable to the RF generator 5 through the switch 4 by cables 105 and 106. The electrode 9 is also configured to be connectable to the RF generator 5 through the switch 4 by cables 107 and 106. Accordingly, FIG. 11 illustrates a RF circuit comprising the RF generator 5, a RF controller (not shown), the switch 4, the electrode 8, the electrode 9, the electrode 10, the capacitor 19, and cables 105, 106, 107 and 108 as the functional portion of the RF circuit to perform a surgical procedure or operation on a subject.

As shown in FIG. 11 when connected to the surgical RE energy generator 5 through the switch 4, the electrode 8 may form a bipolar sealing or coagulating device with the electrode 10. Therefore, the dc circuit may be turned on to remove or reduce the smoke particles when the RF circuit is switched on to perform tissue sealing or coagulation at a surgical site of a subject. When connected to the surgical RF energy generator 5 through the switch 4, the electrode 9 may be used as a cutting blade and the electrode 10 may be used as a return current pad in the RF circuit. Consequently, the dc circuit may be turned on to remove or reduce the smoke particles when the RF circuit is switched on to perform tissue cutting at a surgical site of a subject. The switch 4 may be configured to enable the electrode 9 to perform tissue cutting and to also enable the electrodes 8 and 10 to perform tissue sealing or coagulation at the same time. Consequently, the dc circuit may be turned on to remove or reduce the smoke particles when the RF circuit is switched on to perform tissue cutting and coagulation at a surgical site of a subject. The dc circuit may be turned on simultaneously, concurrently, alternatively, intermittently, or sequentially when the RF circuit is switched on to perform the tissue cutting or the coagulating.

In accordance with FIG. 11, the block 11 containing the electrodes 7, 8, 9 and 10 may be configured to form an insertable front portion of the device or system. Again, the materials and methods suitable for making the electrodes 7, 8, 9 and 10 are well understood in the art for tissue cutting, sealing or coagulation as similarly described for a device of FIG. 1.

In accordance with FIG. 11, the block 6 containing the dc power source 1 and the RF power source 5 may form separate parts configured to be connectable with the block 11 through a plug/socket system or other means that are well understood by a skilled person in the art. The plug/socket system may also include additional hand switches and/or foot pedals whenever desired or necessary.

Figure 12:
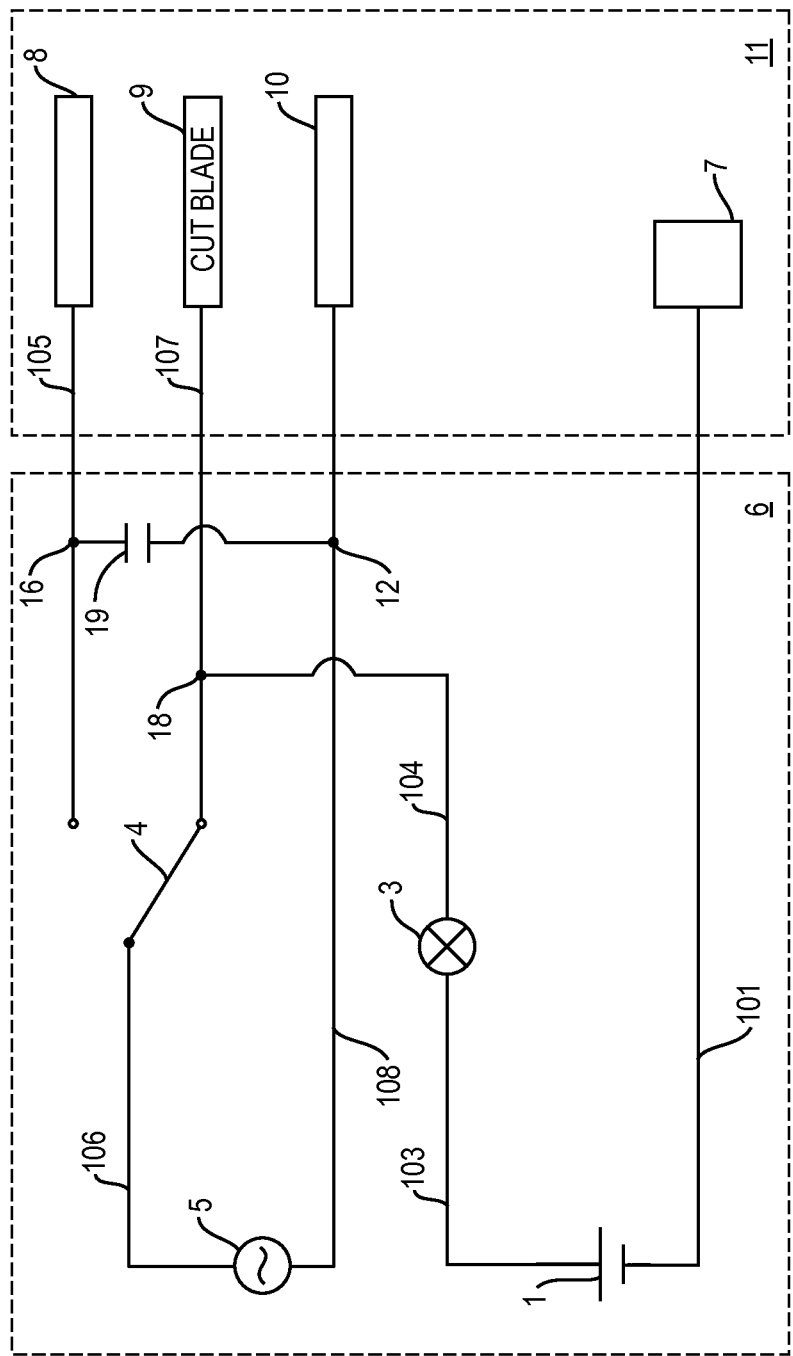
FIG. 12 is a schematic representation of a device or system in accordance with one embodiment of the present disclosure wherein the source of the high voltage dc electricity is disposed separately from the electrodes, and additionally, there is a capacitor between the two sealing electrodes in the RF circuit.

FIG. 12 shows another variation of a device or system in accordance with one embodiment of the present disclosure. The device contains a dc circuit and a RF circuit. The dc circuit includes a high voltage do electrical source 1, a dc power controller (not shown), a RF isolation transformer 3, a first electrode 7, and a second electrode 9. The electrode 7 is configured to be connectable to the high voltage dc electrical source 1 through an insulated conductor or wiring line 101. As previously described, the dc power controller may generally be placed anywhere in the dc circuit so long as it can effectively and efficiently control the voltage and/or current whenever it is needed or desirable. Similarly, the RF isolation transformer may also be placed anywhere in the dc circuit even though FIG. 12 shows it is placed between the electrode 9 and the dc electrical source 1. Consequently, FIG. 12 illustrates a dc circuit comprising the dc electrical source 1, the first electrode 7, the second electrode 9, and cables 101, 103, 104, and 107 as the functional portion of the do circuit to perform smoke particle ionization and removal or reduction of the ionized smoke particles generated at a surgical site. It will be understood that the dc circuit of FIG. 12 performs smoke particle reduction or removal in ways similar to what was previously described for FIG. 1. It will also be understood that the dc circuit may contain as many additional switches or controls as necessary to control or monitor the dc circuit.

The RF circuit in accordance with FIG. 12 includes a radio frequency energy generator 5, a third electrode 8, a fourth electrode 10, a switch 4, and the electrode 9. Consequently, the electrode 9 is configured to be included both in the dc circuit and in the RF circuit. More particularly, it is configured to be connectable with the RF circuit through the switch 4. Also included in the RF circuit is a capacitor 19 placed between the electrode 8 and the electrode 10. Further included in the RE circuit is a RF current and voltage controller (not shown) which may be placed any place in the RF circuit. The electrode 8 is configured to be connectable to the surgical RF energy generator 5 through the switch 4 by cables 105 and 106. Accordingly, FIG. 12 illustrates a RF circuit comprising the surgical RE energy generator 5, a RF controller (not shown), the switch 4, the electrode 8, the electrode 9, the electrode 10, the capacitor 19, and cables 105, 106, 107 and 108 as the functional portion of the RF circuit to perform a surgical procedure or operation on a subject.

As shown in FIG. 12 when connected to the surgical RF energy generator 5 through the switch 4, the electrode 8 may form a bipolar sealing or coagulating device with the electrode 10. Therefore, the dc circuit may be turned on to remove or reduce the smoke particles when the RF circuit is switched on to perform tissue sealing or coagulation at a surgical site of a subject. When connected to the surgical RF energy generator 5 through the switch 4, the electrode 9 may be used as a cutting blade and the electrode 10 may be used as a return current pad in the RF circuit. Consequently, the dc circuit may be turned on to remove or reduce the smoke particles when the RF circuit is switched on to perform tissue cutting at a surgical site of a subject. The dc circuit may be turned on simultaneously, concurrently, alternatively, intermittently, or sequentially when the RE circuit is switched on to perform the tissue cutting or the coagulating.

In accordance with FIG. 12, the block 11 containing the electrodes 7, 8, 9 and 10 may be configured to form an insertable front portion of the device or system. Again, the materials and methods suitable for making the electrodes 7, 8, 9 and 10 are well understood in the art for tissue cutting, sealing or coagulation, ionization, or particle collection as similarly described for a device of FIG. 1.

In accordance with FIG. 12, the block 6 containing the dc power source 1 and the RF power source 5 may form separate parts configured to be connectable with the block 11 through a plug/socket system or other means that are well understood by a skilled person in the art. The plug/socket system may also include additional hand switches and/or foot pedals whenever desired or necessary.

Figure 13:
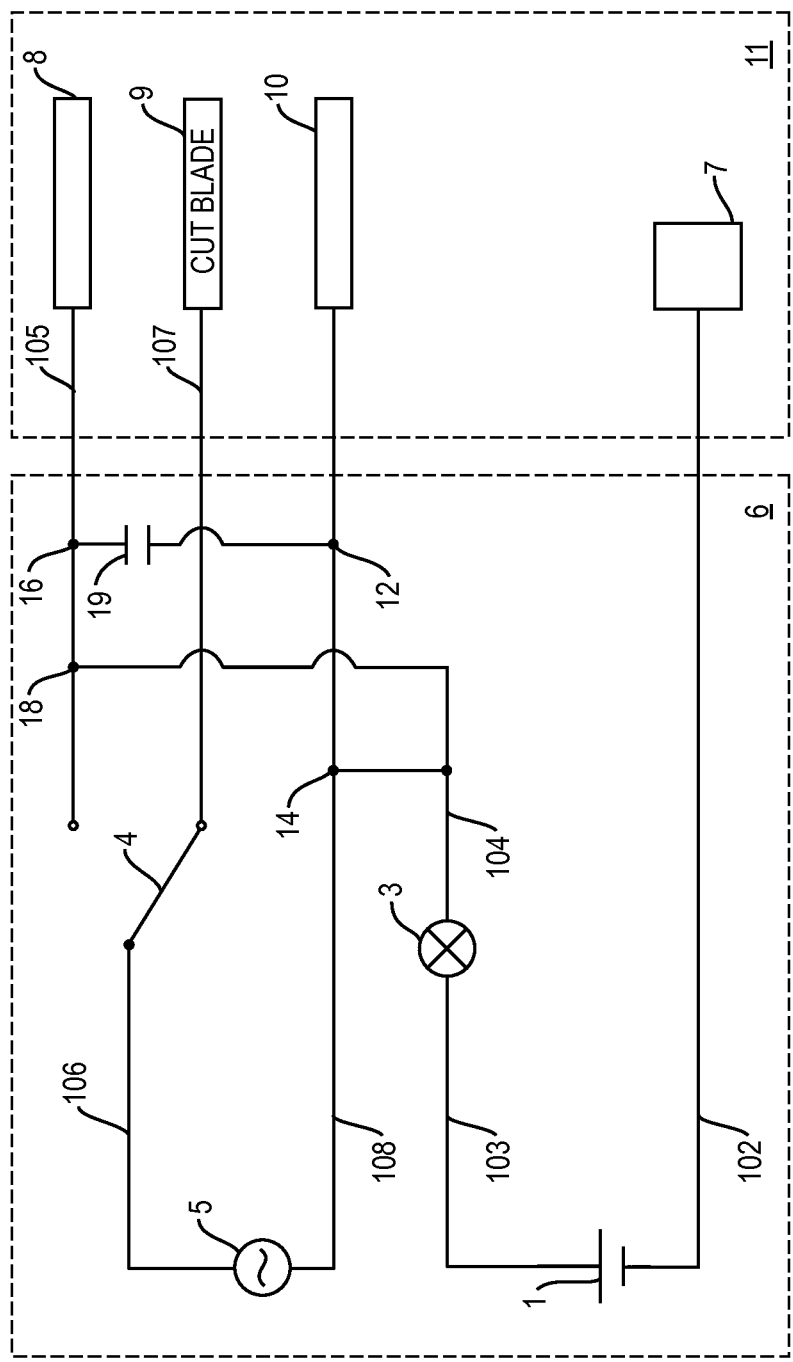
FIG. 13 is a schematic representation of a device or system in accordance with one embodiment of the present disclosure wherein the source of the high voltage dc electricity is disposed separately from the electrodes, and additionally, both sealing electrodes in the RF circuit are configured to be used as one of the two electrodes in the dc circuit.

FIG. 13 shows another variation of a device or system in accordance with one aspect of the present invention. The device contains a dc circuit and a RF circuit. The dc circuit includes high voltage dc electrical source 1, a dc power controller (not shown), a RF isolation transformer 3, a first electrode 7, a second electrode 8, and a third electrode 10. The electrode 7 is configured to be connectable to the high voltage dc electrical source 1 through an insulated conductor or wiring line 101. As previously described, the dc power controller may be placed anywhere in the dc circuit so long as it can effectively and efficiently control the voltage and/or current whenever it is needed or desirable. Similarly, the RF isolation transformer 3 may also be placed anywhere in the dc circuit even though FIG. 13 shows it is placed between the dc electrical source 1 through cable 103 and the electrodes 8 and 10 through cable 104. Consequently, FIG. 12 illustrates a dc circuit comprising the dc electrical source 1, the first electrode 7, the second electrode 8, the third electrode 10, and cables 102, 103, 104, and 105 as the functional portion of the dc circuit to perform smoke particle ionization and removal or reduction of the ionized smoke particles generated at a surgical site. It will be understood that the dc circuit of FIG. 13 performs smoke particle reduction or removal in ways similar to what was previously described for FIG. 1. It will also be understood that the dc circuit may contain as many additional switches or controls as necessary to control or monitor the dc circuit.

The RF circuit in accordance with FIG. 13 includes a radio frequency energy generator 5, a fourth electrode 9, the second electrode 8, the third electrode 10, and a switch 4. As a result, both the electrode 8 and the electrode 10 are configured to be included in the dc circuit and in the RF circuit as well. Also included in the RF circuit is a capacitor 19 between the electrode 8 and the electrode 10. Further included in the RE circuit is a RF current and voltage controller (not shown) which may be placed any place in the RF circuit. The electrode 8 is configured to be connectable to the RF generator 5 through the switch 4 by cables 105 and 106. The electrode 9 is also configured to be connectable to the RF generator 5 through the switch 4 by cables 107 and 106. Accordingly, FIG. 13 illustrates a RF circuit comprising the RF generator 5, a RF controller (not shown), the switch 4, the electrode 8, the electrode 9, the electrode 10, the capacitor 19, and cables 105, 106, 107 and 108 as the functional portion of the RF circuit to perform a surgical procedure or operation on a subject.

As shown in FIG. 13 when connected to the surgical RF energy generator 5 through the switch 4, the electrode 8 may form a bipolar sealing or coagulating device with the electrode 10. Therefore, the dc circuit may be turned on to remove or reduce the smoke particles when the RF circuit is switched on to perform tissue sealing or coagulation at a surgical site of a subject. When connected to the surgical RF energy generator 5 through the switch 4, the electrode 9 may be used as a cutting blade and the electrode 10 may be used as a return current pad in the RF circuit. Consequently, the dc circuit may be turned on to remove or reduce the smoke particles when the RF circuit is switched on to perform tissue cutting at a surgical site of a subject. The dc circuit may be turned on simultaneously, concurrently, alternatively, intermittently, or sequentially when the RF circuit is switched on to perform the tissue cutting or the coagulating.

In accordance with FIG. 13, the block 11 containing the electrodes 7, 8, 9 and 10 may be configured to form an insertable front portion of the device or system. The materials and methods suitable for making the electrodes 7, 8, 9 and 10 are well understood in the art for tissue cutting, sealing or coagulation, ionization, and particle collection as similarly described for a device of FIG. 1.

In accordance with FIG. 13, the block 6 containing the dc power source 1 and the RF power source 5 may form separate parts configured to be connectable with the block 11 through a plug/socket system or other means that are well understood by a skilled person in the art. The plug/socket system may also include additional hand switches and/or foot pedals whenever desired or necessary.

Figure 14:
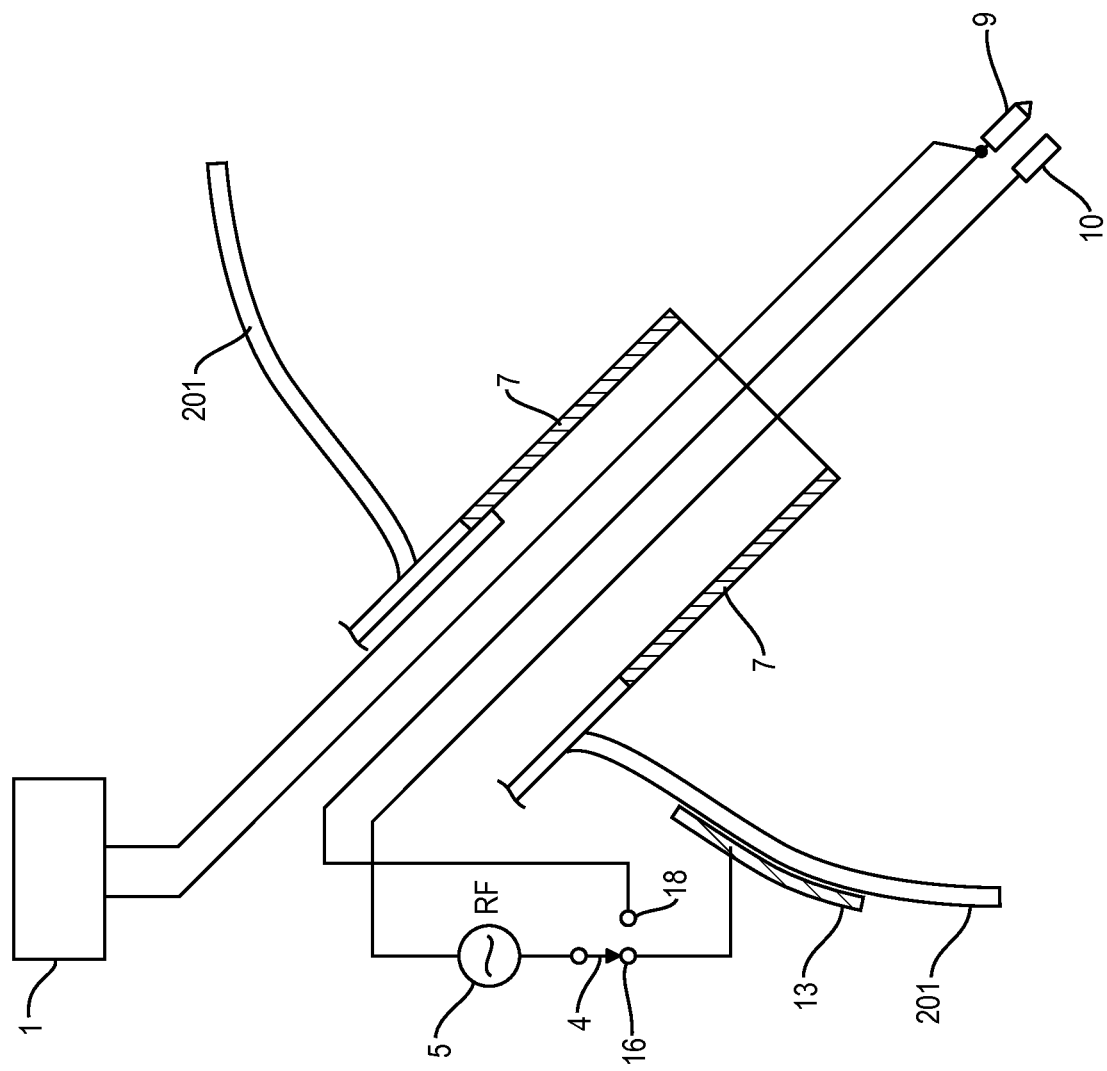
FIG. 14 is a schematic representation of a device or system in accordance with one embodiment of the present disclosure arranged in an operation for the removal or reduction of smoke particles generated during a surgical procedure or operation at a site such as the abdomen of a subject.

FIG. 14 shows another variation of a device or system in accordance with one aspect of the present disclosure when it is desired to remove or reduce smoke particles from a surgical site such as the abdomen of a subject. The system in accordance with FIG. 14 comprises a dc circuit and a RF circuit. The dc circuit comprises a high voltage dc electrical source box 1, an electrode 9, and an electrode 7. The dc electrical source box 1 may be configured to include a dc electrical source, a current/voltage controller, and a RF isolation transformer. The box 1 may be configured to be disposed in the handle portion of the device, or it may be configured to be detachable from the device. The dc circuit may be powered by a battery pack if the box 1 is configured to be disposed in the handle portion of the device. The RF circuit comprises a RF energy source 5, an electrode 10, a RF current return pad 13, the electrode 9, and a switch 4. As a result, the electrode 9 is configured to be in the dc circuit and also in the RF circuit as well. The electrodes 7, 9, and 10 are configured to form the insertable portion of the device. The device is inserted through a cannula (not shown) into a surgical site such as the abdomen region 201 of a subject. Additionally, both the dc circuit and the RF circuit may contain additional switches or controllers as necessary to control or monitor the dc circuit and the RE circuit. The electrode 9 is to be made to possess a ship tip as similarly described for the electrode 9 of FIG. 1 in order to have efficient ionization capability. The electrode 7, configured to be a particle collecting patch for the ionized smoke particles in the dc circuit, is to be made to possess large surface area. FIG. 14 illustrates the electrode 7 is configured to cover the outer surface of the insertable portion of the device. The electrode 10 may be made to possess a large surface area since it may be configured as the return electrode in a bipolar cutting mode for the RF circuit.

When it is desired to use a device of FIG. 14 as a monopolar cutting device, the electrode 9 may be connected with the return patch 13 through the switch 4 to form a monopolar cutting device. The return current pad 13 may be placed under the outside skin of a subject. When it is desired to use a device of FIG. 14 as a bipolar cutting device, the electrode 9 may be connected with the electrode 10 also through the switch 4 to form a bipolar cutting device. The electrode 10 is then used as the return pad. Additionally or alternatively, the electrode 9 may be configured to comprise two subset electrodes 9a and 9b. The electrode 9a may be configured to be an ionization electrode and also a cutting blade. The electrode 9b may be configured to form a bipolar sealing device with the electrode 10.

When it is desired to remove or reduce smoke particles from a surgical site such as the abdomen of a subject by a device of FIG. 14, the high voltage dc supply box 1 can be switched on and a stream of electrons would then be generated round around the tip of the electrode 9. The effect of these electrons around electrode 9 is to ionize any particles or matter suspended around the surgical site. Once the smoke particles are ionized, they will be attracted to the positively charged patch 7. The dc power supply box 1 may be turned on concurrently, simultaneously, sequentially, alternatively, or intermittently with the surgical procedure or operation.

Figure 15:
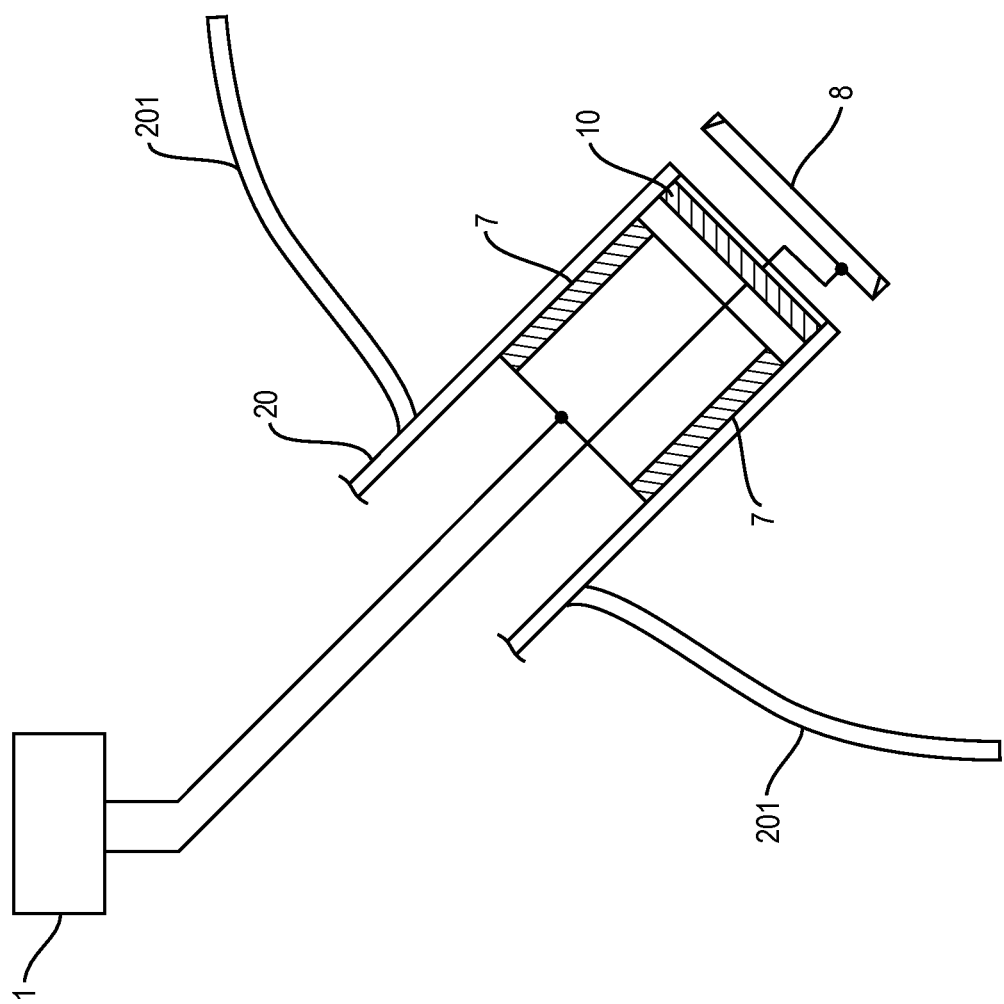
FIG. 15 is a schematic representation of a device in accordance with another embodiment of the present disclosure arranged in an operation for the removal or reduction of smoke particles generated during a surgical procedure or operation at a site such as the abdomen of a subject.

FIG. 15 shows another variation of a device in accordance with one aspect of the present disclosure when it is desired to remove or reduce smoke particles from a surgical site such as the abdomen of a subject. More particularly, a device in accordance with FIG. 15 is a simplified representation of a stand-alone smoke extractor. The device contains a dc circuit comprising a dc power supply box 1 in which a high voltage dc electrical source is housed, a first electrode 8, and a second electrode 7. The electrode 7 is configured to cover the outer surface of the insertable portion of the device. The electrode 7 may be further covered with an outer layer with small holes or pores to allow ionized particles to get through the outer layer to be attracted to the electrode 7. The outer layer should be made with materials that will facilitate the extractor's insertion through a cannula, an access sheath or other tools to a surgical site such as the abdomen of a subject. The electrode 8 may be configured to be a circular electrode that is capable of ionizing smoke particles at a surgical site after it is connected to a high voltage dc electrical source. The connecting line between the electrode 8 and the box 1 may be configured to not only electrically connect the electrode 8 with the dc power source box 1, but also to be strong enough to allow the electrode 8 to be movable along the longitudinal direction. The extractor optionally further comprises a filter 10 which may be used to filter smoke particles.

The smoke extractor is insertable through a tool such as cannula into a surgical site such as the abdomen region 201 of a subject. The dc power supply box 1 may be configured to include a dc electrical source, a RF isolation transformer, and a dc voltage/current controller. Additionally, it may also contain other switches or controllers as necessary to monitor the dc circuit.

Figure 16:
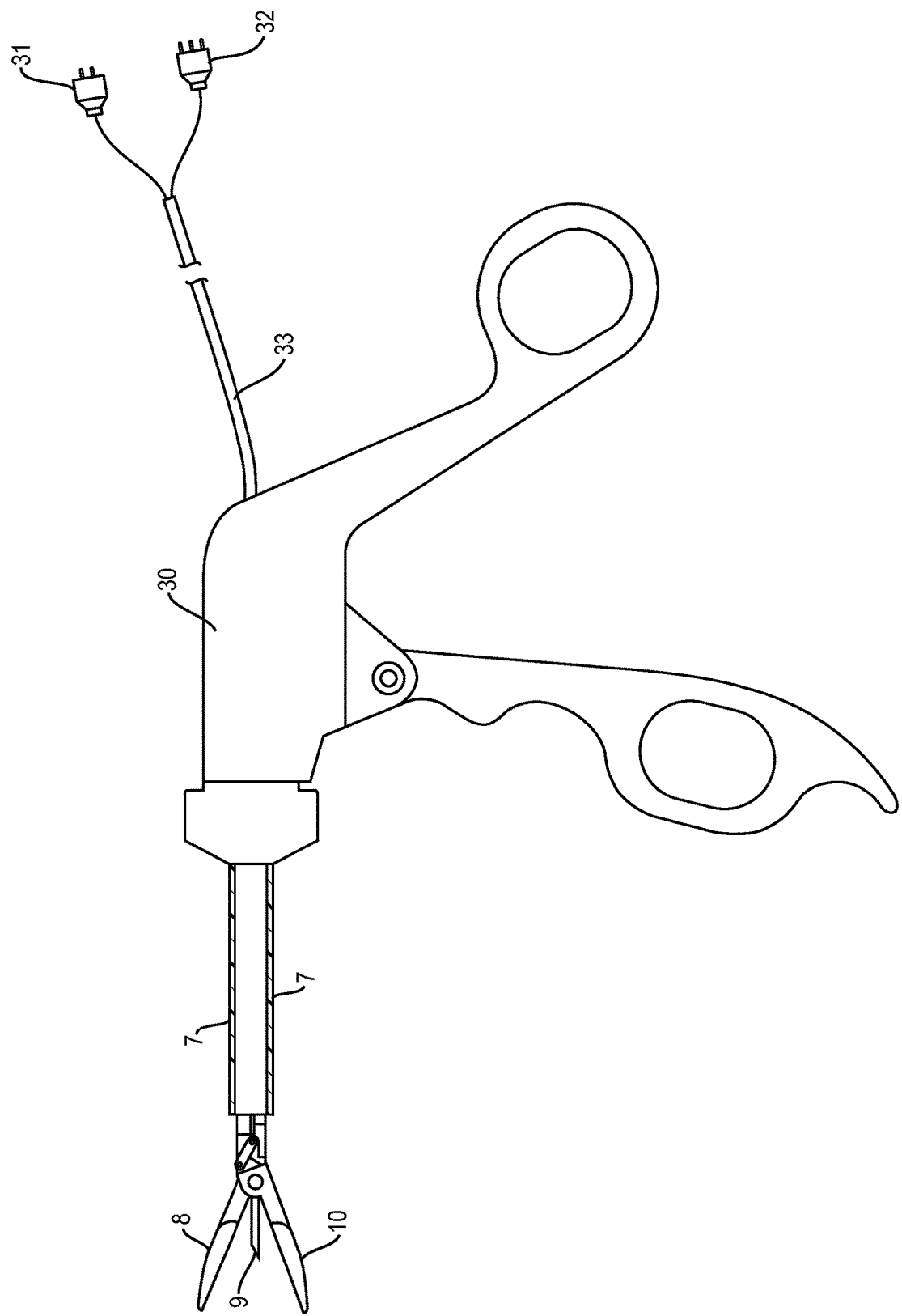
FIG. 16 is another schematic representation of a device in accordance with one embodiment of the present disclosure wherein the two electrodes of the dc circuit and the two electrodes of the RF circuit are all disposed in the insertable portion of the device.

FIG. 16 shows another variation of a device in accordance with one aspect of the present disclosure. The device contains a dc circuit comprising a first electrode 7, a second electrode 9, and wire conductors insulated from one another (not shown), extending through the lumen of the device (not shown) to form an insulating plug-like insert 31 which facilitates a coupling of the device with a high voltage dc electrical source (not shown). The device also contains a RF circuit comprising a third electrode 8, a fourth electrode 10, and wire conductors insulated from one another (not shown), extending also through the lumen of the device to form an insulating plug-like insert 32 which facilitates a coupling of the device with a surgical RF energy source (not shown). The switches or controllers for monitoring or controlling the dc circuit and/or the RF circuit may be disposed on the handle 30 (not shown). More particularly, a dc circuit controller, a RF isolation transformer may be disposed in the handle 30 portion.

In accordance with FIG. 16, the electrode 9 of the device is intended to be used as an ionizing electrode in the dc circuit to ionize smoke particles generated at a site of a surgical procedure or operation, while the electrode 7 is intended to be used to attract and to collect the ionized smoke particles. Under this circumstance, the electrode 7 should be made to possess a large surface area. Consequently, the electrode 7 may be made to partially or wholly cover the outer surface of the tubular member of the device. The electrode 7 may be made with any known conductive materials suitable for such purpose such as nickel gauze which can be washed after use, a mat of conductive material such as random plastic fibers coated in conductive carbon slurry, or a metallic plate.

In accordance with FIG. 16, the electrode 9 of the device is also intended to be used as a cutting blade in the RF circuit. It may be configured to perform a nonopolar cutting with an external return pad (not shown), or perform a bipolar cutting with either the electrode 8 or the electrode 10 or both as a return pad. The electrode 8 and the electrode 10 may be configured to perform bipolar tissue sealing or cauterization.

Additionally or alternatively, a device in accordance with FIG. 16 may not need to have a plug-like insert 31 for coupling with a high voltage dc electrical source if a battery pack is desired to be disposed inside the handle 30 to power the dc circuit (not shown). When a battery pack is contemplated to be disposed inside the handle 30, the first electrode 7 and the second electrode 9 may be connected to the battery pack through insulated wire conductors inside the lumen of the insertable portion of the device (not shown).

In accordance with FIG. 16, the electrodes 7, 8, 9, and 10 are configured to form the insertable portion of the device. Their sizes, dimensions, ratios and/or materials may be made in accordance with the specific needs of the device. Moreover, what is shown in FIG. 16 does not reflect their respective ratios or scales for those electrodes. It should rather be understood that they are merely for illustration purpose.

It should be understood that a device or system in accordance with any one embodiment as described above may also be arranged or adapted to reduce or remove smoke particles from an extracorporeal surgical site. It may also be incorporated with other tools, devices or apparatus. Consequently, the present disclosure is not limited to only incorporate the surgical tools as described herein. It is contemplated that other surgical tools may be incorporated into the multifunctional device or system. Additionally or alternatively, the multifunctional device described herein may be used in combination with other tools such as ultrasonic devices, laser devices and cryosurgical devices.

The contents of all references, patents, pending patent applications and published patents, cited throughout this application are hereby expressly incorporated by reference.

While preferred embodiments of the present disclosure have been shown and described herein, it will be obvious to those skilled in the art that such embodiments are provided by way of example only. Numerous variations, changes, and substitutions will occur to those skilled in the art without departing from the disclosure. It should be understood that various alternatives to the embodiments of the disclosure described herein may be employed. It is intended that the following claims define the scope of the disclosure and that methods and structures within the scope of these claims and their equivalents be covered thereby.

What is claimed:

1. A medical device comprising:
   a first electrode electrically coupled to a first pole of a source of high voltage dc electricity via a first cable, the first electrode electrically coupled to a first pole of a source of surgical radio frequency (RF) energy via a second cable to form a radio frequency circuit to perform a surgical procedure on a subject, wherein the first cable is electrically coupled to the second cable at a connecting node; and
   a second electrode electrically coupled to a second pole of the source of high voltage dc electricity via a third cable, wherein the second pole is opposite the first pole to form a dc circuit to ionize, and remove or reduce smoke particles generated at a surgical site on a subject,
   a third electrode configured to be in electrical communication with a second pole of the source of surgical RF energy; and
   a fourth electrode and a switch, the switch located between the source of surgical RF energy and the second and fourth electrodes, the switch to electrically connect either the second electrode or the fourth electrode to the source of surgical RF energy,
   wherein the third electrode and the fourth electrode are arms of a forceps device, and
   wherein the first electrode is configured to be positioned in the surgical site during the surgical procedure.

2. The medical device of claim 1, wherein the first electrode is configured to be used both as an ionizing electrode in the dc circuit and as a cutting electrode in the radio frequency circuit.

3. The medical device according to claim 1, wherein the medical device comprises:
a handle member, and
the source of high voltage dc electricity,
wherein the source of high voltage dc electricity is located inside of the handle member.

4. The medical device according to claim 3, wherein the source of high voltage dc electricity is provided by a battery pack.

5. The medical device according to claim 1, wherein the medical device comprises a handle, the first electrode and the second electrode are disposed in the handle.

6. The medical device according to claim 1, wherein the medical device comprises a handle member, the first electrode is disposed in the handle.

7. The medical device according to claim 6, wherein the third electrode is disposed in the handle.

8. The medical device according to claim 7, wherein the first electrode and the third electrode comprise a bipolar sealing device.

9. The medical device according to claim 7, wherein the first pole of the source of high voltage dc electricity is a positive pole and the second pole of the source of high voltage dc electricity is a negative pole.

10. The medical device according to claim 7, wherein the second electrode is disposed in the handle.

11. The medical device according to claim 1, comprising:
an isolation transformer electrically coupled between the source of high voltage dc electricity and the first electrode.

12. The medical device according to claim 1, comprising:
a filter to filter the smoke particles.

* * * * *

UNITED STATES PATENT AND TRADEMARK OFFICE
CERTIFICATE OF CORRECTION

PATENT NO.         : 11,020,166 B2
APPLICATION NO.    : 14/865420
DATED              : June 1, 2021
INVENTOR(S)        : Batchelor et al.

It is certified that error appears in the above-identified patent and that said Letters Patent is hereby corrected as shown below:

On the Title Page

Page 2, Column 2, Line 2, delete "2018" and insert --2019-- therefor

Page 2, Column 2, Line 18, delete "Reiection" and insert --Rejection-- therefor

Page 2, Column 2, Line 45, delete ""Europen" and insert --"European-- therefor

Page 2, Column 2, Line 47, delete "Applicatian" and insert --Application-- therefor Signed and Sealed this
Fourteenth Day of September, 2021

Drew Hirshfeld
*Performing the Functions and Duties of the*
*Under Secretary of Commerce for Intellectual Property and*
*Director of the United States Patent and Trademark Office*